(12) United States Patent
Nesvadba et al.

(10) Patent No.: US 6,664,353 B2
(45) Date of Patent: Dec. 16, 2003

(54) HETEROCYCLIC ALKOXYAMINES AS REGULATORS IN CONTROLLED RADICAL POLYMERIZATION PROCESSES

(75) Inventors: Peter Nesvadba, Marly (CH); Andreas Kramer, Düdingen (CH); Marie-Odile Zink, Mulhouse (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/191,193

(22) Filed: Jul. 9, 2002

(65) Prior Publication Data

US 2003/0125494 A1 Jul. 3, 2003

Related U.S. Application Data

(62) Division of application No. 09/417,538, filed on Oct. 14, 1999, now Pat. No. 6,479,608.

(30) Foreign Application Priority Data

Oct. 16, 1998 (EP) .............................. 98811030

(51) Int. Cl.[7] .................................. C08F 2/00
(52) U.S. Cl. ..................... 526/217; 526/328; 526/328.5
(58) Field of Search ................. 526/217, 328, 526/328.5

(56) References Cited

U.S. PATENT DOCUMENTS 3,532,703 A   10/1970  Murayama et al. ......... 260/294
4,581,429 A   4/1986   Solomon et al. ............ 526/220
6,353,107 B1  3/2002   Kramer et al. .............. 546/216

FOREIGN PATENT DOCUMENTS

| EP | 0135280 | 3/1985 |
|----|---------|--------|
| EP | 0735052 | 10/1996 |
| EP | 0869137 | 10/1998 |
| GB | 1145470 | 3/1969 |
| GB | 1337291 | 11/1973 |
| GB | 2361235 | 10/2001 |
| WO | 96/24620 | 8/1996 |
| WO | 98/13392 | 4/1998 |
| WO | 98/30601 | 7/1998 |
| WO | 98/44008 | 10/1998 |

OTHER PUBLICATIONS

Chem. Abstr. 94:175052 for Synthesis (1981), (1), 40–2, Title: Hindered Amine.
Chem. Abstr. 76:47253 for JP 46002905 (1971).
A. Khalaj et al., Monatshefte für Chemie, vol. 128, pp. 395–398, (1997).
Braslau et al., Macromolecules 1997, 30, pp. 6445–6450.

*Primary Examiner*—Helen L. Pezzuto
(74) *Attorney, Agent, or Firm*—Tyler A. Stevenson

(57) ABSTRACT

The present invention is aimed at a process for controlled polymerization of ethylenically unsaturated monomers in the presence of heterocyclic sterically hindered alkoxyamine compounds. The intermediate N-oxyl derivatives, a composition of the N-oxyl derivatives with ethylenically unsaturated monomers and a free radical initiator, as well as a process for polymerization are also subjects of the present invention. Still further subjects of the invention are novel amine precursors and a novel process for manufacturing 5-ring heterocyclic amines.

21 Claims, No Drawings

HETEROCYCLIC ALKOXYAMINES AS REGULATORS IN CONTROLLED RADICAL POLYMERIZATION PROCESSES

This is a divisional of application Ser. No. 09/417,538, filed on Oct. 14, 1999, now U.S. Pat. No. 6,479,608.

The present invention relates to heterocyclic alkoxyamine compounds, a polymerizable composition comprising a) at least one ethylenically unsaturated monomer and b) a heterocyclic alkoxyamine compound. Further aspects of the present invention are a process for polymerizing ethylenically unsaturated monomers, and the use of heterocyclic alkoxyamine compounds for controlled polymerization. The intermediate N-oxyl derivatives, a composition of the N-oxyl derivatives with ethylenically unsaturated monomers and a free radical initiator, as well as a process for polymerization are also subjects of the present invention. Further subjects of the invention are novel amine precursors and a novel process for manufacturing 5-ring heterocyclic amines.

The compounds of the present invention provide polymeric resin products having low polydispersity. The polymerization process proceeds with enhanced monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

Polymers or copolymers prepared by free radical polymerization processes inherently have broad molecular weight distributions or polydispersities which are generally higher than about four. One reason for this is that most of the free radical initiators have half lives that are relatively long, ranging from several minutes to many hours, and thus the polymeric chains are not all initiated at the same time and the initiators provide growing chains of various lengths at any time during the polymerization process. Another reason is that the propagating chains in a free radical process can react with each other in processes known as combination and disproportionation, both of which are irreversibly chain-terminating reaction processes. In doing so, chains of varying lengths are terminated at different times during the reaction process, resulting in resins consisting of polymeric chains which vary widely in length from very small to very large and which thus have broad polydispersities. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O• groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

WO 98/13392 describes open chain alkoxyamine compounds which have a symmetrical substitution pattern and are derived from NO gas or from nitroso compounds.

EP-A-735 052 discloses a method for preparing thermoplastic polymers of narrow polydispersities by free radical-initiated polymerization, which comprises adding a free radical initiator and a stable free radical agent to the monomer compound.

WO 96/24620 describes a polymerization process in which very specific stable free radical agents are used, such as for example

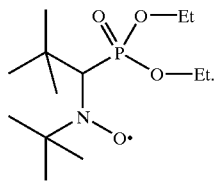

WO 98/30601 discloses specific nitroxyls based on imidazolidinons. Nitroxylethers are generically mentioned but not specifically disclosed.

WO 98/44008 discloses specific nitroxyls based on morpholinones, piperazinones and piperazindiones. The nitroxylethers are also generically mentioned but not specifically disclosed.

Despite the above mentioned attempts to improve the control of radical polymerization reactions there is still a need for new polymerization regulators, which are highly reactive, and give an equally good or better control of the molecular weight of the polymer.

Surprisingly it has been found that particularly 5 and 6 membered heterocyclic alkoxyamines or their nitroxyl precursors, which have a high sterical hindrance in α-position to the alkoxyamine group lead to regulators/initiators which allow polymerization very efficient and fast at higher temperatures, but also work at relatively low temperatures such as for example 100° C. The higher sterical hindrance may be introduced by at least one higher alkyl substituent than methyl in α-position to the alkoxyamine group. In many cases even higher hindrance by two, three or four higher alkyl groups may be advantageous. The higher sterical hindrance may be also advantageous for 7 and 8 membered heterocyclic alkoxyamines or their nitroxyl precursors.

One subject of the present invention is a polymerizable composition, comprising
a) at least one ethylenically unsaturated monomer or oligomer, and b) a compound of formula (Ia) or (Ib)

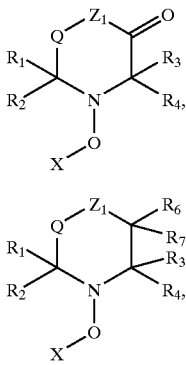

(Ia)

(Ib)

wherein $R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;

with the proviso that if Q in formula (Ia) is a direct bond, —$CH_2$— or CO, at least one of $R_1$, $R_2$, $R_3$ or $R_4$ is different from methyl;

$R_5$, $R_6$ and $R_7$ independently are hydrogen, $C_1$–$C_{18}$alkyl or $C_6$–$C_{10}$aryl;

X represents a group having at least one carbon atom and is such that the free radical X• derived from X is capable of initiating polymerization of ethylenically unsaturated monomers;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$CC_{18}$alkenyl, $C_3$–$C_{18}$alkinyl which are substituted by one or more OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl;

with the proviso that the compounds (A) and (B) are excluded (A)

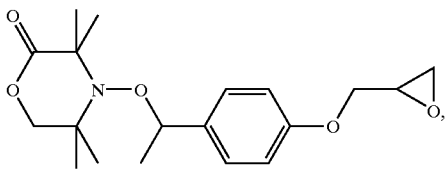

(B)

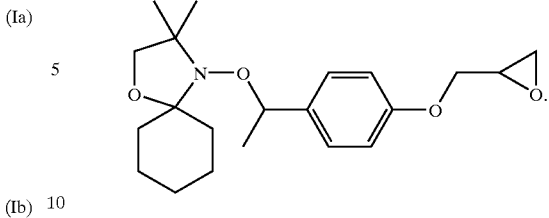

Halogen is F, Cl, Br or I, preferably Cl or Br.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Alkenyl with 3 to 18 carbon atoms is a linear or branched radical as for example propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl oder n-4-octadecenyl. Preferred is alkenyl with 3 bis 12, particularly preferred with 3 to 6 carbon atoms.

Alkinyl with 3 to 18 is a linear or branched radical as for example propinyl

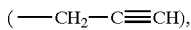

2-butinyl, 3-butinyl, n-2-octinyl, oder n-2-octadecinyl. Preferred is alkinyl with 3 to 12, particularly preferred with 3 to 6 carbon atoms.

Examples for hydroxy substituted alkyl are hydroxy propyl, hydroxy butyl or hydroxy hexyl.

Examples for halogen substituted alkyl are dichloropropyl, monobromobutyl or trichlorohexyl.

$C_2$–$C_{18}$alkyl interrupted by at least one O atom is for example —$CH_2$—$CH_2$—O—$CH_2$—$CH_3$, —$CH_2$—$CH_2$—O—$CH_3$— or —$CH_2$—$CH_2$—O—$CH_2$—$CH_2$—$CH_2$—O—$CH_2$—$CH_3$—. It is preferably derived from polyethylene glycol. A general description is —(($CH_2$)$_a$—O)$_b$—H/$CH_3$, wherein a is a number from 1 to 6 and b is a number from 2 to 10.

$C_2$–$C_{18}$alkyl interrupted by at least one $NR_5$ group may be generally described as —(($CH_2$)$_a$—$NR_5$)$_b$—H/$CH_3$, wherein a, b and $R_5$ are as defined above.

$C_3$–$C_{12}$cycloalkyl is typically, cyclopropyl, cyclopentyl, methylcyclopentyl, dimethylcyclopentyl, cyclohexyl, methylcyclohexyl or trimethylcyclohexyl.

$C_6$–$C_{10}$ aryl is for example phenyl or naphthyl, but also comprised are $C_1$–$C_4$alkyl substituted phenyl, $C_1$–$C_4$alkoxy substituted phenyl, hydroxy, halogen or nitro substituted phenyl. Examples for alkyl substituted phenyl are ethylbenzene, toluene, xylene and its isomers, mesitylene or isopropylbenzene. Halogen substituted phenyl is for example dichlorobenzene or bromotoluene.

The $C_1$–$C_4$alkoxy substituents are methoxy, ethoxy, propoxy or butoxy and their corresponding isomers.

$C_7$–$C_9$phenylalkyl is benzyl, phenylethyl or phenylpropyl.

$C_5$–$C_{10}$heteroaryl is for example pyrrol, pyrazol, imidazol, 2,4, dimethylpyrrol, 1-methylpyrrol, thiophene, furane, furfural, indol, cumarone, oxazol, thiazol, isoxazol, isothiazol, triazol, pyridine, α-picoline, pyridazine, pyrazine or pyrimidine.

Preferred is a composition according, wherein in formula (Ia) and (Ib) $R_1$, $R_2$, $R_3$ and $R_4$ independently of each other are $C_1$–$C_6$alkyl, which is unsubstituted or substituted by OH, halogen or a group —O—C(O)—$R_5$, $C_2$–$C_{12}$alkyl which is interrupted by at least one O atom and/or $NR_5$ group, $C_5$–$C_6$cycloalkyl or $C_6$–$C_{10}$aryl or $R_1$ and $R_2$ and/or $R_3$ and $R_4$ together with the linking carbon atom form a $C_5$–$C_6$cycloalkyl radical.

More preferred is a composition, wherein in formula (Ia) and (Ib) $R_1$, $R_2$, $R_3$ and $R_4$ independently of each other are $C_1$–$C_4$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical; and
$R_5$ is hydrogen or $C_1$–$C_4$alkyl.

Preferrably in formula (Ia) and (Ib) $R_6$ and $R_7$ independently are hydrogen, methyl or ethyl.

Preferably in formula (Ia) and (Ib) $R_8$ is hydrogen, $C_1$–$C_{18}$alkyl, $C_1$–$C_{18}$alkyl which is substituted by OH; or $C_7$–$C_9$phenylalkyl.

More preferably in formula (Ia) and (Ib) $R_8$ is hydrogen, $C_1$–$C_4$alkyl, $C_1$–$C_4$alkyl which is substituted by OH; phenyl or benzyl.

Preferred is a composition, wherein in formula (Ia) and (Ib) $R_9$, $R_{10}$, $R_{11}$, $R_{12}$, $R_{13}$ and $R_{14}$ are independently hydrogen or $C_1$–$C_4$alkyl.

Preferred is a composition, wherein in formula (Ia) and (Ib) Q is a direct bond or a divalent radical $CH_2$, $CH_2$—$CH_2$, $CH_2$—$CH_2$—$CH_2$, C(O) or $CH_2$C(O), $CH_2$—CH—$CH_3$, $CH_2$—CH-phenyl, phenyl-CH—$CH_2$—CH-phenyl, phenyl-CH—$CH_2$—CH—$CH_3$, $CH_2$—CH($CH$)$_3$—$CH_2$, $C(CH_3)_2$—CH-phenyl or $C(CH_3)_2$—$CH_2$—CH—$CH_3$.

Preferably in formula (Ia) and (Ib) X is selected from the group consisting of —CH(aryl)$_2$, —$CH_2$-aryl,

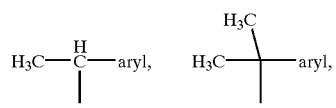

($C_5$–$C_6$cycloalkyl)$_2$CCN, $C_5$–$C_6$cycloalkylidene-CCN, ($C_1$–$C_{12}$alkyl)$_2$CCN, —$CH_2$CH=$CH_2$, ($C_1$–$C_{12}$)alkyl-$CR_{30}$—C(O)—($C_1$–$C_{12}$)alkyl, ($C_1$–$C_{12}$)alkyl-$CR_{30}$—C(O)—($C_6$–$C_{10}$)aryl, ($C_1$–$C_{12}$)alkyl-$CR_{30}$—C(O)—($C_1$–$C_{12}$)alkyl, ($C_1$–$C_{12}$)alkyl-$CR_{30}$—C(O)-phenoxy, ($C_1$–$C_{12}$)alkyl-$CR_{30}$—C(O)—N-di($C_1$–$C_{12}$)alkyl, ($C_1$–$C_{12}$)alkyl-$CR_{30}$—CO—NH($C_1$–$C_{12}$)alkyl, ($C_1$–$C_{12}$)alkyl-$CR_{30}$—CO—$NH_2$, —$CH_2$CH=CH—$CH_3$, —$CH_2$—$C(CH_3)$=$CH_2$, —$CH_2$—CH=CH-aryl,

—$CH_2$—C≡CH,

—O—C(O)—$C_1$–$C_{12}$alkyl, —O—C(O)—($C_6$–$C_{10}$)aryl, ($C_1$–$C_{12}$)alkyl-$CR_{30}$—CN,

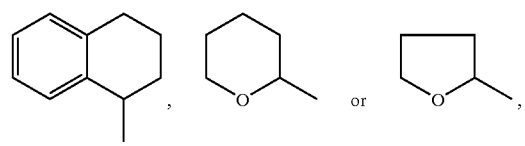

wherein
$R_{30}$ is hydrogen or $C_1$–$C_{12}$alkyl; and
the aryl groups are phenyl or naphthyl which are unsubstituted or substituted with $C_1$–$C_{12}$alkyl, halogen, $C_1$–$C_{12}$alkoxy, $C_1$–$C_{12}$alkylcarbonyl, glycidyloxy, OH, —COOH or —COO$C_1$–$C_{12}$alkyl.

Aryl is preferably phenyl, which is unsubstituted or substituted as described above.

More preferred is a composition, wherein in formula (Ia) and (Ib) X is selected from the group consisting of —$CH_2$-phenyl, $CH_3$CH-phenyl, $(CH_3)_2$C-phenyl, $(CH_3)_2$CCN, —$CH_2$CH=$CH_2$, $CH_3$CH—CH=$CH_2$ and O—C(O)-phenyl.

A preferred subgroup of compounds are those of formula (Ia) and (Ib), wherein $R_1$, $R_2$, $R_3$ and $R_4$ independently of each other are $C_1$–$C_3$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical;
$R_5$ is hydrogen or $C_1$–$C_4$alkyl.
$R_6$ and $R_7$ independently are hydrogen, methyl or ethyl;
$Z_1$ is O or $NR_8$;
Q is a direct bond or a divalent radical $CH_2$, $CH_2CH_2$, $CH_2$—$CH_2$—$CH_2$, C(O), $CH_2$C(O) or $CH_2$—CH—$CH_3$.
$R_8$ is hydrogen, $C_1$–$C_4$alkyl, $C_1$–$C_4$alkyl which is substituted by OH, or benzyl; and
X is selected from the group consisting of $CH_2$-phenyl, $CH_3$CH-phenyl, $(CH_3)_2$C-phenyl, $(CH_3)_2$CCN, $CH_2$CH=$CH_2$, $CH_3$CH—CH=$CH_2$.

Another preferred composition is, wherein in formula (Ia) and (Ib) at least two of $R_1$, $R_2$, $R_3$ and $R_4$ are ethyl, propyl or butyl and the remaining are methyl.

Another preferred subgroup is wherein at least three of $R_1$, $R_2$, $R_3$ and $R_4$ are ethyl, propyl or butyl.

The other substituents are as defined above including their preferences.

Particularly preferred is a composition, wherein the compound is of formula (Ic), (Id), (Ie), (If), (Ig) or (Ih)

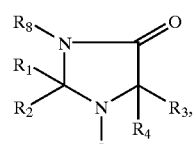
(Ic)

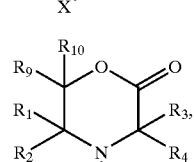
(Id)

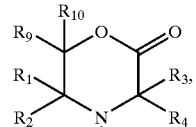
(Ie)

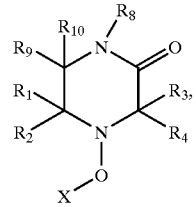
(If)

-continued (Ig)

(Ih)

wherein $R_1$ to $R_{12}$ and X have the meaning as defined above including their preferences.

Within the above subgroup the compounds of formula (Id), (Ie), (Ig) or (Ih) are particularly preferred.

A further preferred subgroup within the compounds of formulae (Ic)–(Ih) are those, wherein $R_1$, $R_2$, $R_3$ and $R_4$ independently of each other are $C_1$–$C_3$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical;

$R_5$ is hydrogen or $C_1$–$C_4$alkyl.

$R_6$ and $R_7$ independently are hydrogen, methyl or ethyl;

$R_8$ is hydrogen, $C_1$–$C_4$alkyl, $C_1$–$C_4$alkyl which is substituted by OH, or benzyl;

$R_9$, $R_{10}$, $R_{11}$ and $R_{12}$ are independently hydrogen or $C_1$–$C_4$alkyl; and X is selected from the group consisting of $CH_2$-phenyl, $CH_3CH$-phenyl, $(CH_3)_2C$-phenyl, $(CH_3)_2CCN$, $CH_2CH{=}CH_2$, $CH_3CH{-}CH{=}CH_2$.

More preferred are those, wherein the compound is of formula (Ie);

$R_1$, $R_2$, $R_3$ and $R_4$ independently of each other are $C_1$–$C_3$alkyl, which is unsubstituted or substituted by OH, or a group —O—C(O)—$R_5$, $R_5$ is hydrogen or $C_1$–$C_4$alkyl.

$R_8$ is hydrogen, $C_1$–$C_4$alkyl, $C_1$–$C_4$alkyl which is substituted by OH, or benzyl;

$R_9$ and $R_{10}$ are hydrogen; and

X is selected from the group consisting of $CH_2$-phenyl, $CH_3CH$-phenyl, $(CH_3)_2C$-phenyl, $(CH_3)_2CCN$, $CH_2CH{=}CH_2$, $CH_3CH{-}CH{=}CH_2$.

Preferably the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl) acrylic acidanhydrides, (alkyl)acrylic acid salts, (alkyl) acrylic esters, (meth)acrylonitriles, (alkyl)acrylamides, vinyl halides or vinylidene halides.

Preferred ethylenically unsaturated monomers are ethylene, propylene, n-butylene, i-butylene, isoprene, 1,3-butadiene, $\alpha$-$C_5$–$C_{18}$alkene, styrene, $\alpha$-methyl styrene, p-methyl styrene or a compound of formula $CH_2{=}C(R_a)$—$(C{=}Z)$—$R_b$, wherein $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino, —O—$CH_2$—$CH_2$—$N(CH_3)_2$ or —O—$CH_2$—$CH_2$—$N^+H(CH_3)_2An^-$;

$An^-$ is a anion of a monovalent organic or inorganic acid;

Me is a monovalent metal atom or the ammonium ion.

Z is oxygen or sulfur.

Examples of acids from which the anion $An^-$ is derived are $C_1$–$C_{12}$carboxylic acids, organic sulfonic acids such as $CF_3SO_3H$ or $CH_3SO_3H$, mineralic acids such as HCl, HBr or HI, oxo acids such as $HClO_4$ or complex acids such as $HPF_6$ or $HBF_4$.

Examples for $R_a$ as $C_2$–$C_{100}$alkoxy interrupted by at least one O atom are of formula $$R_c{-}O{-}\!\left[\!\underset{\phantom{.}}{\overset{R_d}{-}}\!O\right]_{\!v}\!-,$$

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

wherein $An^-$ and $R_a$ have the meaning as defined above and $R_e$ is methyl or benzyl. $An^-$ is preferably $Cl^-$, $Br^-$ or $^-O_3S$—$CH_3$.

Further acrylate monomers are

-continued

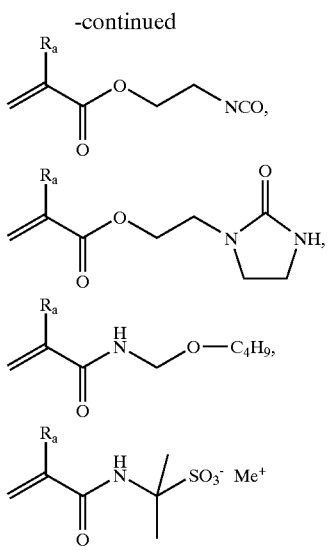

Examples for suitable monomers other than acrylates are

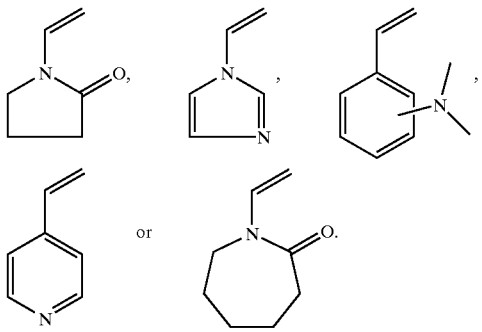

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide or dimethylaminopropyl-methacrylamide.

It is also possible to enhance the rate of polymerization or copolymerization of slowly polymerizing monomers such as for example of the class of methacrylates, in particular methylmethacrylate by the addition of more readily polymerizable comonomers such as acrylates. Typical examples are the polymerization or copolymerization of methylmethacrylate in the presence of methylacrylate or butylacrylate.

Typical slowly polymerizing methacrylates are methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, methacrylamide or dimethylaminopropyl-methacrylamide. The polymerization of these methacrylates can be enhanced by the addition of the corresponding acrylates.

Also preferred is a composition, wherein the ethylenically unsaturated monomer is a mixture of a methacrylate and an acrylate.

The amounts of readily polymerizable comonomers range typically from 5 parts to 95 and the slowly polymerizable monomers range from 95 to 5 parts respectively.

The compound of formula (Ia) or (Ib) is preferably present in an amount of from 0.01 mol-% to 30 mol-%, more preferably in an amount of from 0.05 mol-% to 20 mol-%, and most preferably in an amount of from 0.1 mol-% to 10 mol-% based on the monomer or monomer mixture.

Another subject of the invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula (Ia) or (Ib) as described above under reaction conditions capable of effecting scission of the O—X bond to form two free radicals, the radical •X being capable of initiating polymerization.

Preferably the scission of the O—X bond is effected by ultrasonic treatment, heating or exposure to electromagnetic radiation, ranging from γ to microwaves.

More preferably the scission of the O—X bond is effected by heating and takes place at a temperature of between 50° C. and 160° C., more preferably between 80° C. and 150° C.

After the polymerization step is completed the reaction mixture may be cooled down to a temperature below 60° C., preferably to room temperature. The polymer may be stored at this temperature without further reactions occuring.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%. In many cases it is possible to polymerize without any solvent.

If organic solvents are used, suitable solvents or mixtures of solvents are typically pure alkanes (hexane, heptane, octane, isooctane), aromatic hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are usefull as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systeme, as coating additives (e.g. rheological agents, compatibilizers, reactive diluents) or as resin component in coatings(e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2 000 to 250 000 g/mol and, more preferably, from 2 000 to 200 000 g/mol. The number average molecular weight may be determined by size exclusion chromatography (SEC), matrix assisted laser desorption/ionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.1 to 2, more preferably of from 1.2 to 1.8.

Thus, the present invention also encompasses in the synthesis novel block, multi-block, star, gradient, random, hyperbranched and dendritic copolymers, as well as graft copolymers.

The polymers prepared by the present invention are useful for following applications:
adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macromolecules 1996, Vol 29, No. 12, pages 4167–4171, graft (co) polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

Another subject of the present invention is a polymer or oligomer having attached at least one initiator group —X and at least one oxyamine group of formula (Xa) or (Xb)

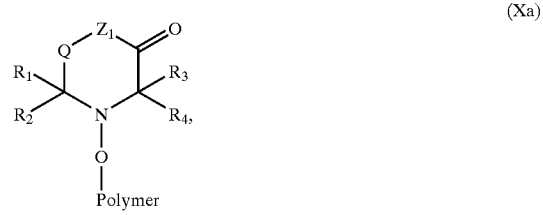

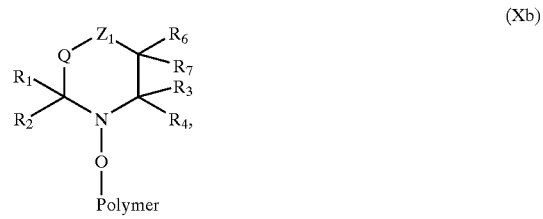

wherein $R_1$ to $R_7$, Q and $Z_1$ are as defined above including their preferences.

The majority of compounds of formula (Ia) and (Ib) is novel and they are consequently also subject of the present invention.

The new compounds are of formula (IIa) or (IIb)

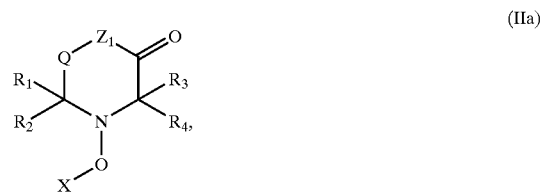

-continued (IIb)

wherein $R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;

with the proviso that if Q in formula (Ia) is a direct bond, —$CH_2$— or CO, at least one of $R_1$, $R_2$, $R_3$ or $R_4$ is different from methyl;

$R_5$, $R_6$ and $R_7$ independently are hydrogen, $C_1$–$C_{18}$alkyl or $C_6$–$C_{10}$aryl;

X is selected from the group consisting of —CH(aryl)$_2$, —$CH_2$-aryl,

—$CH_2$—$CH_2$-aryl, ($C_5$–$C_6$cycloalkyl)$_2$CCN, $C_5$–$C_6$cycloalkylidene-CCN, ($C_1$–$C_{12}$alkyl)$_2$CCN, —$CH_2CH$=$CH_2$, ($C_1$–$C_{12}$)alkyl-$CR_{30}$—C(O)—($C_1$–$C_{12}$)alkyl, ($C_1$–$C_{12}$)alkyl-$CR_{30}$—C(O)—($C_6$–$C_{10}$)aryl, ($C_1$–$C_{12}$)alkyl-$CR_{30}$—C(O)—($C_1$–$C_{12}$)alkoxy, ($C_1$–$C_{12}$)alkyl-$CR_{30}$—C(O)-phenoxy, ($C_1$–$C_{12}$)alkyl-$CR_{30}$—C(O)—N-di($C_1$–$C_{12}$)alkyl, ($C_1$–$C_{12}$)alkyl-$CR_{30}$—CO—NH($C_1$–$C_{12}$)alkyl, ($C_1$–$C_{12}$)alkyl-$CR_{30}$—CO—$NH_2$, —$CH_2CH$=CH—$CH_3$, —$CH_2$—C($CH_3$)=$CH_2$, —$CH_2$—CH=CH-phenyl, —O—C(O)—$C_1$–$C_{12}$alkyl, —O—C(O)—($C_6$–$C_{10}$)aryl, ($C_1$–$C_{12}$)alkyl-$CR_{30}$—CN, wherein
$R_{30}$ is hydrogen or $C_1$–$C_{12}$alkyl;
$Z_1$ is O or $NR_8$;
$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}$C(O), wherein $R_9$, $R_{10}$, $R_{11}$, $R_{12}$, $R_{13}$ and $R_{14}$ are independently hydrogen, phenyl or $C_1$–$C_{18}$alkyl; and the aryl groups are phenyl or naphthyl which are unsubstituted or substituted with $C_1$–$C_{12}$alkyl, halogen, $C_1$–$C_{12}$alkoxy, $C_1$–$C_{12}$alkylcarbonyl, glycidyloxy, OH, —COOH or —COO$C_1$–$C_{12}$alkyl;

with the proviso that the compounds (A) and (B) are excluded (A)

(B)

In particular the compounds are of formula (IIc), (IId), (IIe), (IIf), (IIg) or (IIh)

(IIc)

(IId)

(IIe)

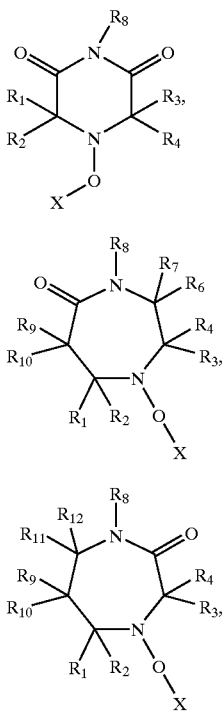

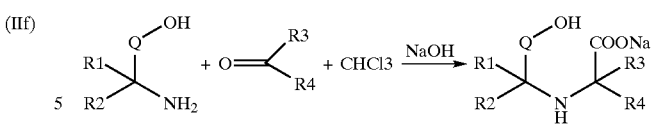 (IIf)

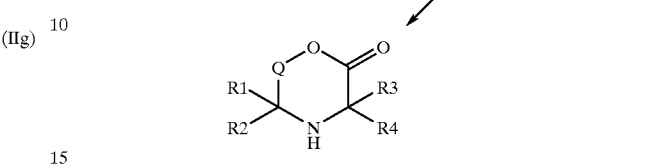 (IIg)

The reaction is described for 6 membered rings by J. T. Lai.: Synthesis, 122 (1984). The meaning of Q is in this case $CR_9R_{10}$.

2. Subgroup.

The compounds of formula

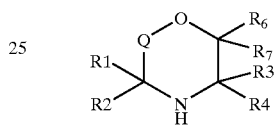

are for example accessible by a ring forming reaction with a diol

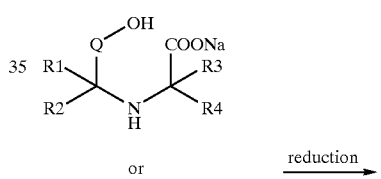

or

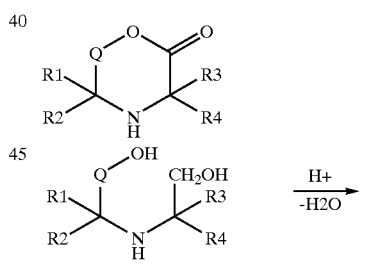

The reaction is described for morpholines by J. T. Lai.: Synthesis, 122 (1984). Q has the meaning $CR_9R_{10}$.

3. Subgroup.

The piperazinones of formula

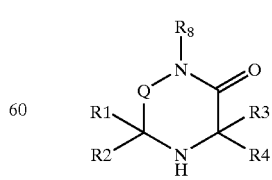

are prepared by reacting a diamine with chloroform and a ketone in the presence of NaOH (J. T. Lai.: Synthesis, 40 (1981). Q is $CR_9R_{10}$.

wherein $R_1$ to $R_{12}$ have the meaning as defined above and X is selected from the group consisting of —$CH_2$-phenyl, $CH_3CH$-phenyl, $(CH_3)_2C$-phenyl, $(CH_3)_2CCN$, —$CH_2CH=CH_2$, $CH_3CH—CH=CH_2$ and O—C(O)-phenyl.

Examples of the different substituents including their preferences have already been given with regard to the composition and apply also for the compounds of formula (IIa) and (IIb).

The compounds of formula (Ia), (Ib), (IIa) or (IIb) in general may be prepared according to standard methods, starting from the corresponding N—H compound, from which the corresponding N—O• compounds are prepared, and which are further reacted to the corresponding N—O—X compounds. A detailed description is outlined below.

Summary of suitable methods for the preparation of the amine (N—H) precursors.

1. Subgroup

The compounds of formula

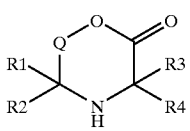

are for example accessible by reacting an amino alcohol with a ketone and for example chloroform under basic conditions. The resulting hydroxycarboxylate is subsequently reacted to the cyclic lactone

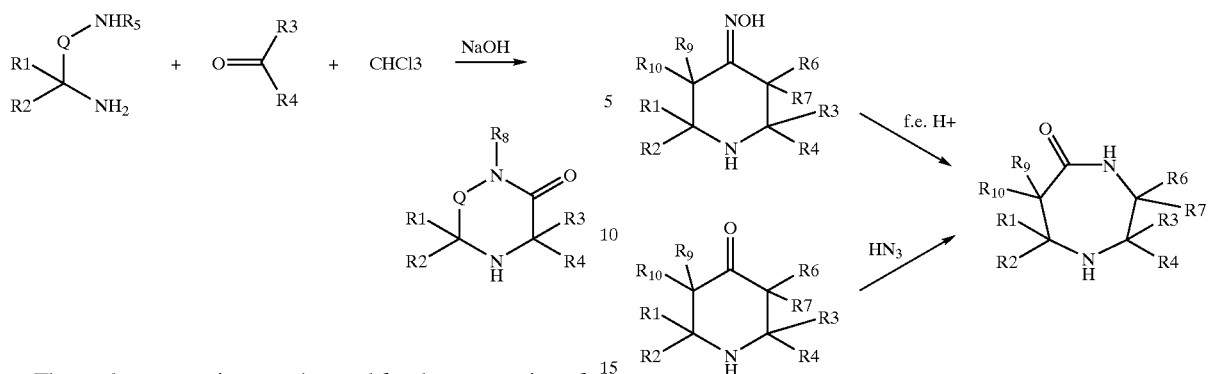

The analogue reaction may be used for the preparation of 7 membered rings (Pyong-nae Son et al.: J. Org. Chem. 46, 323 (1981). Q is $CH_2$—$CR_9R_{10}$.

4. Subgroup.

6-membered rings (piperazindione) of formula

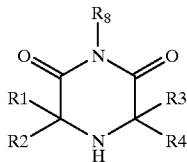

may for example prepared from aminodinitriles according to E. F. J. Duynstee et al.: Recueil 87, 945 (1968).

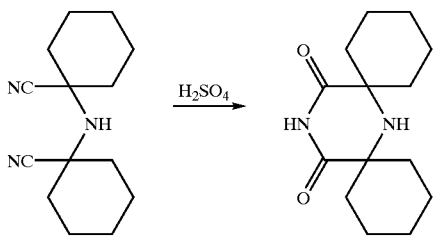

5. Subgroup.

The lactames of formula

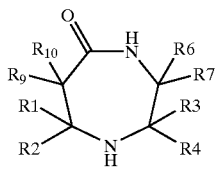

may be prepared by Beckmann rearrangement of the corresponding oximes. Another possibility is the Schmidt-Reaction as described by S. C. Dickermann et. al.: J. Org. Chem. 14, 530, (1949)):

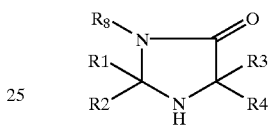

6. Subgroup.

The preparation of compounds of formula

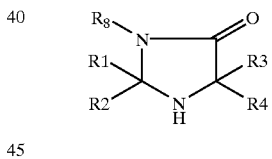

is for example described by T. Toda et. al.: Bull. Chem. Soc. Japan, 44, 3445 (1971) or by Te-Chen Tsao et al.: Biotechnol. Prog. 7, 60 (1991).

However the known methods lead only to compounds wherein only two of $R_1$, $R_2$, $R_3$ or $R_4$ are higher alkyl than methyl.

A further subject of the present invention is therefore a process for the preparation of a compound of formula (Vc)

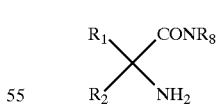

wherein $R_1$, $R_2$, $R_3$ and $R_4$ are independently $C_1$–$C_{18}$alkyl, with the proviso that at least 3 are other than methyl and $R_8$ is as defined above; by reacting a 1,1-dialkylglycinamide of formula (XXI)

(XXI)

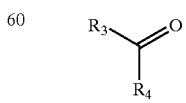

with a ketone of formula XXII under acid catalysis in an inert solvent to a compound of formula (Vc)

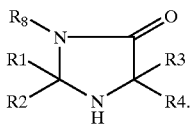
(IVc)

The reaction is typically carried out in excess of the corresponding ketone or an inert solvent. Suitable solvents or mixtures of solvents are typically pure alkanes (hexane, heptane, octane, isooctane), aromatic hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

Typical acid catalysts are mineral acids like HCl, $H_2SO_4$, $BF_3$, acidic ion-exchanger resins, acidic clays and montmorilonites or strong organic acids like oxalic acid.

The reaction is carried out under normal pressure at a temperature ranging from room temperature to the boiling temperature of the reaction mixture.

Typically the reaction time is 1 to 100 h, preferably 1 to 20 hours.

The N—H precursors of the corresponding N—O—X compounds of formula (Ia) and (Ib) are partly new.

The new compounds are therefore also subject of the present invention. Subject of the invention is a compound of formula (IVa) or (IVb)

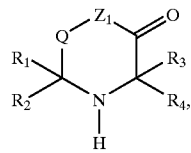
(IVa)

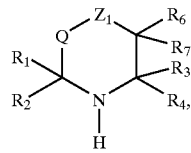
(IVb)

wherein
$R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl;
$R_5$, $R_6$ and $R_7$ independently are hydrogen, $C_1$–$C_{18}$alkyl or $C_6$–$C_{10}$aryl;
$Z_1$ is O or $NR_8$;
$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;
Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C$(O), wherein $R_9$, $R_{10}$, $R_{11}$, $R_{12}$, $R_{13}$ and $R_{14}$ are independently hydrogen, phenyl or $C_1$–$C_{18}$alkyl;

with the proviso that if the compounds of formula (IVa) or (IVb) represent a 5, 6 or 7 membered ring at least two of $R_1$, $R_2$, $R_3$ and $R_4$ are different from methyl and the substitution patterns $R_1$, $R_2$, $R_3$, $R_4$ being methyl, methyl, butyl, butyl or methyl, ethyl, methyl, ethyl are excluded.

Preferred is a compound, wherein $R_1$, $R_2$, $R_3$ and $R_4$ independently of each other are $C_1$–$C_4$alkyl, which is unsubstituted or substituted by OH, or a group —O—C(O)—$R_5$, with the proviso that if the compounds of formula (IVa) or (IVb) represent a 5, 6 or 7 membered ring at least two of $R_1$, $R_2$, $R_3$ and $R_4$ are different from methyl and the substitution patterns methyl methyl, butyl, butyl or methyl, ethyl, methyl, ethyl are excluded;
$R_5$ is hydrogen or $C_1$–$C_4$alkyl.
$R_6$ and $R_7$ independently are hydrogen, methyl or ethyl;
$Z_1$ is O or $NR_8$;
Q is a direct bond or a divalent radical $CH_2$, $CH_2CH_2$, $CH_2$—$CH_2$—$CH_2$, C(O), $CH_2C$(O) or $CH_2$—CH—$CH_3$;
$R_8$ is hydrogen, $C_1$–$C_4$alkyl or $C_1$–$C_4$alkyl which is substituted by OH, or benzyl.

More preferred is a compound wherein at least three of $R_1$, $R_2$, $R_3$ and $R_4$ are different from methyl.

Examples of the different substituents including their preferences have already been given and apply also for the compounds of formula (IVa) and (IVb).

As already mentioned the compounds of formula (IVa) and (IVb) are precursors which are oxidized to the corresponding N—O• compounds.

The oxidation of amines to the corresponding nitroxides is well known and a review is given for example by L. B. Volodarsky, V. A. Reznikov, V. I. Ovcharenko.: Synthetic Chemistry of Stable Nitroxides, CRC Press, Boca Raton 1994.

The N—O• precursors of the corresponding N—O—X compounds of formula (Ia) and (Ib) are also partly new.

These new compounds are therefore also subject of the present invention.

A further subject of the invention is a compound of formula (IIIa) or (IIIb)

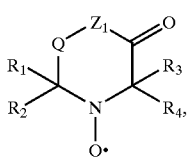
(IIIa)

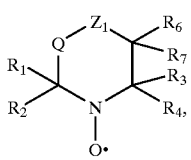
(IIIb)

wherein
$R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;
$R_5$, $R_6$ and $R_7$ independently are hydrogen, $C_1$–$C_{18}$alkyl or $C_6$–$C_{10}$aryl;
$Z_1$ is O or $NR_8$;
$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl;

with the proviso that in formula (IIIa)

if Q is a direct bond and $Z_1$ is $NR_8$, at least three of $R_1$, $R_2$, $R_3$ or $R_4$ are higher alkyl than methyl;

or if Q is $CH_2$ and $Z_1$ is O, at least one of $R_1$, $R_2$, $R_3$ or $R_4$ is higher alkyl than methyl;

or if Q is $CH_2$ or C(O) and $Z_1$ is $NR_8$ at least two of $R_1$, $R_2$, $R_3$ or $R_4$ are higher alkyl than methyl or one is higher alkyl than methyl and $R_1$ and $R_2$ or $R_3$ and $R_4$ form a $C_3$–$C_{12}$cycloalkyl radical together with the linking carbon atom.

Preferred is a compound, wherein $R_1$, $R_2$, $R_3$ and $R_4$ independently of each other are $C_1$–$C_4$alkyl, which is unsubstituted or substituted by OH or a group —O—C(O)—$R_5$; $R_5$ is hydrogen or $C_1$–$C_4$alkyl.

$R_6$ and $R_7$ independently are hydrogen, methyl or ethyl;

$Z_1$ is O or $NR_8$;

Q is a direct bond or a divalent radical $CH_2$, $CH_2CH_2$, $CH_2$—$CH_2$—$CH_2$, C(O), $CH_2C(O)$ or $CH_2$—CH—$CH_3$;

$R_8$ is hydrogen, $C_1$–$C_4$alkyl or $C_1$–$C_4$alkyl which is substituted by OH, or benzyl; with the proviso that in formula (IIIa)

if Q is a direct bond and $Z_1$ is $NR_8$, at least three of $R_1$, $R_2$, $R_3$ or $R_4$ are higher alkyl than methyl;

or if Q is $CH_2$ and $Z_1$ is O, at least one of $R_1$, $R_2$, $R_3$ or $R_4$ is higher alkyl than methyl;

or if Q is $CH_2$ or C(O) and $Z_1$ is $NR_8$ at least two of $R_1$, $R_2$, $R_3$ or $R_4$ are higher alkyl than methyl or one is higher alkyl than methyl and $R_1$ and $R_2$ or $R_3$ and $R_4$ form a $C_3$–$C_{12}$cycloalkyl radical together with the linking carbon atom.

Examples of the different substituents including their preferences have already been given and apply also for the compounds of formula (IIIa) and (IIIb).

These compounds are intermediates of the title compounds and may also be used together with a radical source to effect polymerization of ethylenically unsaturated monomers or oligomers.

Consequently a further subject of the invention is a polymerizable composition, comprising a) at least one ethylenically unsaturated monomer or oligomer, and b) a compound of formula (IIIa) or (IIIb)

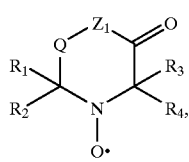

(IIIa)

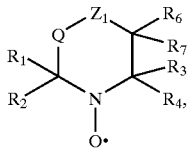

(IIIb)

wherein $R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;

$R_5$, $R_6$ and $R_7$ independently are hydrogen, $C_1$–$C_{18}$alkyl or $C_6$–$C_{10}$aryl;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkinyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl;

with the proviso that in formula (IIIa)

if Q is a direct bond and $Z_1$ is $NR_8$, at least three of $R_1$, $R_2$, $R_3$ or $R_4$ are higher alkyl than methyl;

or if Q is $CH_2$ and $Z_1$ is O, at least one of $R_1$, $R_2$, $R_3$ or $R_4$ is higher alkyl than methyl;

or if Q is $CH_2$ or C(O) and $Z_1$ is $NR_8$ at least two of $R_1$, $R_2$, $R_3$ or $R_4$ are higher alkyl than methyl or one is higher alkyl than methyl and $R_1$ and $R_2$ or $R_3$ and $R_4$ together with the linking carbon atom form a $C_3$–$C_{12}$cycloalkyl radical;

c) a free radical source capable of initiating polymerization of ethylenically unsaturated monomers.

Preferred is a composition, wherein the compound is of formula (IIIc), (IIId), (IIIe), (IIIf), (IIIg) or (IIIh)

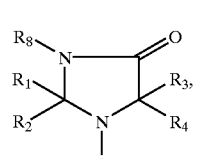

(IIIc)

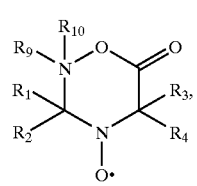

(IIId)

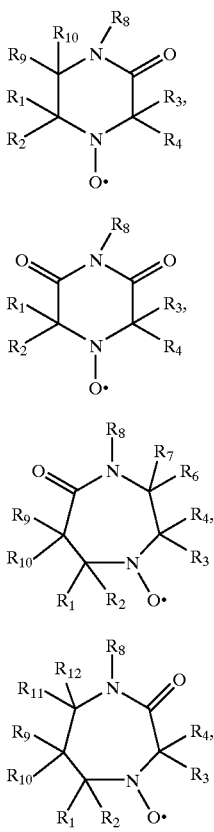

wherein $R_1$ to $R_{12}$ have the meaning as defined defined above.

Examples for the different substituents including their preferences have already been given. They apply also for the compounds in the above composition.

The production of C-centered radicals is described, inter alia, in Houben Weyl, Methoden der Organischen Chemie, Vol. E 19a, pages 60–147. These methods can be applied in general analogy.

The source of radicals may be a bis-azo compound, a peroxide or a hydroperoxide.

Preferably, the source of radicals is 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide.

Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl) peroxide, diisononanoyl peroxide, didecanoyl peroxide, dioctanoyl peroxide, dilauroyl peroxide, bis (2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononanoate, 2,5-dimethylhexane 2,5-dibenzoate, t-butyl peracetate, t-amyl perbenzoate, t-butyl perbenzoate, 2,2-bis (t-butylperoxy) butane, 2,2 bis (t-butylperoxy) propane, dicumyl peroxide, 2,5-dimethylhexane-2,5-di-t-butylperoxide, 3-t-butylperoxy 3-phenylphthalide, di-t-amyl peroxide, α,α'-bis(t-butylperoxy isopropyl) benzene, 3,5-bis (t-butylperoxy)3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

The molar ratio of the radical source to the compound of formulae IIIa or IIIb may be from 1:10 to 10:1, preferably from 1:5 to 5:1 and more preferably from 1:2 to 2:1.

The NOX compounds are prepared for example by reacting the Nitroxides with free radicals. The radicals may be generated by scission of peroxy- or azo compounds as for example described by T. J. Connolly, M. V. Baldovi, N. Mohtat, J. C. Scaiano.: Tet. Lett. 37, 4919 (1996) or by I. Li, B. A. Howell et al.: Polym. Prepr. 36, 469 (1996). Suitable examples are given above.

Another possibility is a halogen atom transfer from a alkylhalogenide in the presence of Cu(I) as described by K. Matyjaszewski.: Macromol. Symp. 111, 47–61 (1996).) or a one electron oxidation as described by P. Stipa, L. Greci, P. Carloni, E. Damiani.: Polym. Deg. Stab. 55, 323 (1997))

Further possibilities are the O-alkylation of the corresponding hydroxylamine, as for example described by Said Oulad Hammouch, J. M. Catala.: Macromol. Rapid Commun. 17, 149–154 (1996), Meisenheinmer rearrangement of the corresponding N-Allyl-N-oxids as described by B. Walchuk et al.: Polymer Preprints 39, 296 (1998) or the reaction of a oxoammonium salt with a carbonyl compound, as described by Tan Ren, You-Cheng Liu, Qing-Xiang Guo.: Bull. Chem. Soc. Jpn. 69, 2935 (1996).

Still further subjects of the invention are the use of a compound of formula (Ia) or (Ib) and the use of a compound of formula (IIIa) or (IIIb) together with a free radical source as defined above for the polymerization of ethylenically unsaturated monomers or oligomers.

The following examples illustrate the invention.

EXAMPLES

5-Ring Compounds

Example A1

1-(1-cyanocyclohexyloxy)-2,5-dicyclohexylidene-imidazolidin-4-one (101)

1.2 g (0.005 mol) of 2,5-dicyclohexylidene-imidazolidin-4-on-1-oxyl (prepared in accordance with T. Toda et al.: Bull. Chem. Soc. Japan 44, 3445 (1971)) and 1.25 g (0.005 mol) of 1,1'-azobis(cyclohexanecarbonitrile) are refluxed for 16 hours under nitrogen in 20 ml of benzene. The benzene is then removed by distillation in a rotary evaporator and the residue is chromatographed over silica gel with dichloromethane/ethyl acetate (19:1). The pure fractions are concentrated to dryness by evaporation, made into a slurry with hexane, filtered and and then dried.

This gives 0.5 g (29%) of compound (101), m.p. 240–242° C. (degradation).

Analysis calculated for $C_{20}H_{31}N_3O_2$: C 69.53%, H 9.04%, N 12.16%; found C 69.32%, H 9.11%, N 12.19%.

Example A2

1-(dimethylcyanomethyloxy)-2,5-diethyl-2,5-dimethylimidazolidin-4-one (102)

3.1 g (0.0167 mol) of 2,5-diethyl-2,5-dimethylimidazolidin-4-on-1-oxyl (prepared in accordance with T. Toda et al.: Bull. Chem. Soc. Japan 44, 3445 (1971)) and 4.1 g (0.0167 mol) of azobisisobutyronitrile are stirred for 17 hours at 75° C. under nitrogen in 20 ml of benzene. The benzene is then removed by distillation in a rotary evaporator and the residue is chromatographed over silica gel with hexane/ethyl acetate (1:1). The pure fractions are concentrated to dryness by evaporation, made into a slurry with hexane, filtered and then dried.

This gives 2.9 g (68.5%) of compound (102), m.p. 118–121° C. (degradation).

Analysis calculated for $C_{13}H_{23}N_3O_2$: C 61.63%, H 9.15%, N 16.59%; found C 61.62%, H 9.15%, N 16.61%.

Example A3

2,2,5,5-tetraethylimidazolidin-4-one (103)

26.5 g (0.2 mol) of 1,1-diethylglycinamide (prepared in accordance with Safir et. al.: J. Amer. Chem. Soc., 77, 4840 (1955)), 70 ml of diethylketone, 1.95 g (0.01 mol) of p-to-luenesulfonic acid and 0.5 ml of n-octylmercaptane are refluxed for 72 hours in a water separator. After cooling, the reaction mixture is washed with water, dried over $MgSO_4$, concentrated by evaporation in a rotary evaporator and recrystallised from hexane.

This gives 30.65 g (77%) of compound (103), m.p. 68–70° C.

Analysis calculated for $C_{11}H_{22}N_2O$: C 66.62%, H 11.18%, N 14.13%; found C 66.41%, H 11.07%, N 14.10%.

Example A4

2,2,5,5-tetraethylimidazolidin-4-on-1-oxyl (104)

A solution of 25.9 g (0.105 mol) of m-chloroperbenzoic acid (70%) in 50 ml of ethyl acetate is added dropwise, with stirring, at 10° C. to a solution of 13.9 g (0.070 mol) of 2,2,5,5-tetraethylimidazolidin-4-one in 75 ml of ethyl acetate. This mixture is stirred for 24 hours at room temperature and is then charged with another 5 g of m-chloroperbenzoic acid (70%) and stirred for 20 hours. Subsequently, it is washed with 3×100 ml of 1M $NaHCO_3$, dried over $MgSO_4$ and concentrated by evaporation in a rotary evaporator. The residue is chromatographed over silica gel with hexane/ethyl acetate (2:1). The pure fractions are concentrated to dryness by evaporation and recrystallised from hexane.

This gives 8.65 g (58%) of compound (104), m.p. 110–112° C.

Analysis calculated for $C_{11}H_{21}N_2O_2$: C 61.94%, H 9.92%, N 13.13%; found C 61.84%, H 10.08%, N 13.04%.

Example A5

1-(dimethylcyanomethyloxy)-2,2,5,5-tetraethylimidazolidin-4-one (105)

4.3 g (0.022 mol) of 2,2,5,5-tetraethylimidazolidin-4-on-1-oxyl and 3.0 g (0.018 mol) of azobisisobutyronitrile are refluxed for 8 hours under nitrogen in 15 ml of benzene. The benzene is then removed by evaporation in a rotary evaporator and the residue is chromatographed over silica gel with hexane/ethyl acetate (3:1). The pure fractions are concentrated to dryness by evaporation and recrystallised from hexane/dichloromethane. This gives 3.95 g (65%) of compound (105), m.p. 125–130° C. (degradation). Analysis calculated for $C_{15}H_{27}N_3O_2$: C 64.03%, H 9.67%, N 14.93%; found C 64.00%, H 9.86%, N 14.94%.

Example A6

1-(α-methylbenzyloxy)-2,2,5,5-tetraethylimidazolidin-4-one (106)

4.14 g (0.019 mol) of 2,2,5,5-tetraethylimidazolidin-4-on-1-oxyl are dissolved in 250 ml of ethylbenzene and charged with 14.3 ml (0.078 mol) of di-tert-butylperoxide. This solution is then irradiated until colourless in a Pyrex photoreactor under nitrogen at room temperature using a mercury lamp. The ethylbenzene is then removed by distillation in a rotary evaporator and the residue is recrystallised from pentane.

This gives 4.96 g (80%) of compound (106), m.p. 153–157° C. (degradation).

Analysis calculated for $C_{19}H_{30}N_2O_2$: C 71.66%, H 9.49%, N 8.80%; found C 71.54%, H 9.58%, N 8.87%.

6-Ring Compounds

Example B1

3-ethyl-3,3,5-trimethylmorpholin-2-on-4-oxyl (204)

A solution of 42.5 g (0.172 mol) of m-chloroperbenzoic acid (70%) in 70 ml of ethyl acetate is added dropwise, with stirring, to a solution of 19.7 g (0.115 mol) of 3-ethyl-3,5,5-trimethylmorpholin-2-one (prepared in accordance with J. T. Lai.: Synthesis 122 (1984)) in 80 ml of ethyl acetate at 10° C. The reaction mixture is stirred for another 12 hours at room temperature and is then washed with 3×120 ml of 1 M $NaHCO_3$ and with water, dried over $MgSO_4$ and concentrated by evaporation in a rotary evaporator. The residue is chromatographed over silica gel with ethyl acetate/hexane (1:2). The pure fractions are concentrated to dryness by evaporation and are recrystallised from hexane.

This gives 19 g (89%) of compound (204), m.p. 48–50° C.

Analysis calculated for $C_9H_{16}NO_3$: C 58.05%, H 8.66%, N 7.52%; found C 58.10%, H 8.70%, N 7.42%.

Example B2

4-(dimethylcyanomethyloxy)-3-ethyl-3,5,5-trimethylmorpholin-2-one (205)

4.1 g (0.022 mol) of 3-ethyl-3,3,5-trimethylmorpholin-2-on-4-oxyl and 2.7 g (0.017 mol) of azobisisobutyronitrile are refluxed under nitrogen in 8 ml of benzene for 2.5 hours. The benzene is then removed by distillation in a rotary evaporator and the residue is chromatographed over silica gel with hexane/ethyl acetate (4:1). The pure fractions are concentrated to dryness by evaporation and are recrystallised from hexane/ethyl acetate.

This gives 5.3 g (96%) of compound (205), m.p. ~71° C.

$^1$H-NMR ($CDCl_3$), d(ppm): 4.17 d (1H), 3.90 d (1H), 1.95 m ($CH_2$), 1.67 s 2×($CH_3$), 1.60 s ($CH_3$), 1.21 s ($CH_3$), 1.20 s ($CH_3$), 1.02 t ($CH_3$), Example B3

4-(α-methylbenzyloxy)-3-ethyl-3,5,5-trimethylmorpholin-2-one (206)

A photoreactor is charged with 210 ml of ethylbenzene, 4.81 g (0.026 mol) of 3-ethyl-3,5,5-trimethyl-morpholin-2- on-4-oxyl and 15.3 g (0.105 mol) of t-butylperoxide. The red solution is rinsed with nitrogen and is then irradiated under nitrogen at 20–25° C. using a mercury dipping lamp (Pyrex coat). After about 8 hours, the solution has lost its colour. The reaction mixture is concentrated by evaporation in a rotary evaporator, resulting in 6.0 g (80%) of the desired compound in the form of a slightly yellow oil.

Elemental analysis calculated for $C_{17}H_{25}NO_3$: C 70.07%; H 8.65%; N 4.81%. Found: C 70.67%; H 8.46%; N 4.53%.

Example B4

3,3-diethyl-5,5-dimethylmorpholin-2-one (207)

120 g (3 mol) of finely ground sodium hydroxide are added, with stirring, to a solution of 53.5 g (0.6 mol) of 2-amino-2-methylpropanol and 73 ml (0.9 mol) of chloroform in 635 ml (6 mol) of diethylketone at 5–10° C. The reaction mixture is stirred at room temperature for 16 hours and is then filtered. The solid is made into a slurry with 2×350 ml of methanol and filtered. The filtrates are concentrated to dryness by evaporation in a rotary evaporator and the residue is charged with 200 ml of 32% hydrochloric acid and 100 ml of water and refluxed for 6 hours. Subsequently, 600 ml of toluene are added and the water is completely removed by distillation in a water separator. 91 ml (0.66 mol) of triethylamine are then added dropwise to the toluene solution and the mixture is refluxed for another 6 hours. The precipitated triethylamine hydrochloride is removed by filtration and the filtrate is subjected to distillation at 123–127° C./20 mbar, giving compound (207) in the form of a colourless liquid, yield 63.7 g (57%).

$^1$H-NMR (CDCl$_3$), d(ppm): 4.11 s (CH$_2$), 1.90–1.60 m 2×(CH$_2$), 1.20 s 2×(CH$_3$), 0.96 t 2×(CH$_3$).

Example B5

3,3-diethyl-5,5-dimethylmorpholin-2-on-4-oxyl (208)

32.2 g (0.165 mol) of peracetic acid (39% in acetic acid) are added dropwise to a solution of 20.4 g (0.110 mol) of 3,3-diethyl-5,5-dimethylmorpholin-2-one in 120 ml of ethyl acetate at 5° C. The reaction mixture is stirred for 6 hours at room temperature and is then washed with 120 ml of 1 M NaHCO$_3$ and with water, dried over MgSO$_4$ and concentrated by evaporation in a rotary evaporator. The residue is recrystallised from hexane.

This gives 20.4 g (92%) of compound (208), m.p. ~63° C.

Analysis calculated for $C_{10}H_{18}NO_3$: C 59.98%, H 9.06%, N 6.99%; found C 59.81%, H 9.07%, N 6.97%.

Example B6

4-(dimethylcyanomethyloxy)-3,3-diethyl-5,5-dimethylmorpholin-2-one (209)

5.0 g (0.025 mol) of 3,3-diethyl-5,5-dimethylmorpholin-2-on-4-oxyl and 3.0 g (0.019 mol) of azobisisobutyronitrile are refluxed for 6.5 hours under nitrogen in 8 ml of benzene. The benzene is then removed by distillation in a rotary evaporator and the residue is recrystallised from hexane/benzene.

This gives 6.15 g (91%) of compound (209), m.p. ~83° C.

$^1$H-NMR (CDCl$_3$), d(ppm): 4.08 d (1H), 3.99 d (1H), 2.2–1.8 m 2×(CH$_2$), 1.67 s 2×(CH$_3$), 1.22 s (CH$_3$), 1.20 s (CH$_3$), 1.02 t 2×(CH$_3$).

Example B7

4-(α-methylbenzyloxy)-3,3-diethyl-5,5-dimethylmorpholin-2-one (210)

In analogy to Example B3, compound (206), 4.75 g (0.026 mol) of 3,3-diethyl-5,5-dimethylmorpholin-2-on-4-oxyl are reacted with t-butylperoxide and ethylbenzene as solvent, resulting in 4.1 g (52%) of compound (210) in the form of a colourless oil.

Elemental analysis calculated for $C_{18}H_{27}NO_3$: C 70.79%; H 8.91%; N 4.59%. Found: C 71.67%; H 8.74%; N 4.46%.

Example B8

3,3,5,5-tetraethylmorpholin-2-one (211)

In analogy to Example B4 (compound 207), 4.35 g (23%) of compound (211) are obtained in the form of a colourless oil from 10.2 g (0.087 mol) of 2-amino-2,2-diethylethanol (prepared in accordance with L. Villa et al.: II Farmaco 23, 441 (1968)), 11 ml (0.13 mol) of chloroform, 92 ml (0.87 mol) of diethylketone and 17.4 g (0.43 mol) of sodium hydroxide.

Analysis calculated for $C_{12}H_{23}NO_2$: C 67.57%, H 10.87%, N 6.57%; found C 67.46%, H 10.91%, N 6.49%.

Example B9

3,3,5,5-tetraethylmorpholin-2-on-4-oxyl (212)

0.05 g of sodium tungstate are added to a solution of 4.2 g (0.02 mol) of 3,3,5,5-tetraethylmorpholin-2-one in 25 ml of ethyl acetate and then 5.85 g (0.03 mol) of peracetic acid (39% in acetic acid) are added dropwise at 5° C. The reaction mixture is stirred for 24 hours at room temperature and is then washed with 1 M NaHCO$_3$ and water, dried over MgSO$_4$ and concentrated by evaporation in a rotary evaporator.

This gives 4.5 g (98%) of compound (212) in the form of a red oil.

Analysis calculated for $C_{12}H_{22}NO_3$: C 63.13%, H 9.71%, N 6.13%; found C 63.13%, H 9.69%, N 6.26%.

Example B10

4-(α-methylbenzyloxy)-3,3,5,5-tetraethylmorpholin-2-one (213)

1.03 g (0.0045 mol) of 3,3,5,5-tetraethylmorpholin-2-on-4-oxyl are dissolved in 200 ml of ethylbenzene and charged with 3.3 ml (0.018 mol) of di-tert-butylperoxide. The solution is irradiated until colourless in a Pyrex photoreactor under nitrogen at room temperature using a mercury lamp. The ethylbenzene is removed by distillation in a rotary evaporator and the residue is chromatographed over silica gel with hexane/ethyl acetate 14:1). The pure fractions are concentrated by evaporation, giving 1.0 g (67%) of compound (213) in the form of a colourless oil.

Analysis calculated for $C_{20}H_{31}NO_3$: C 72.04%, H 9.37%, N 4.20%; found C 71.76%, H 9.35%, N 3.93%.

Example B11

3,3,5-trimethyl-5-pivaloyloxymethylmorpholin-2-on-4-oxyl (214)

A) 3,3,5-trimethyl-5-pivaloyloxymethylmorpholin-2-one

A solution of 2.63 g (0.021 mol) of pivaloyl chloride is added dropwise to a solution of 3.5 g (0.02 mol) of 3,3,5-trimethyl-5-hydroxymethylmorpholin-2-one (prepared in accordance with J. T. Lai.: Synthesis 122 (1984)) and 0.1 g of 4-dimethylaminopyridine in 20 ml of dichloromethane at 15° C. After stirring for 16 hours, another 0.75 ml of pivaloyl chloride is added and the reaction mixture is stirred for 24 hours.

The reaction mixture is washed with 1 M NaHCO$_3$ and water and is then dried over MgSO$_4$ and concentrated by evaporation in a rotary evaporator. The residue is chromatographed over silica gel with hexane/ethyl acetate. The pure fractions are concentrated by evaporation, giving 2.55 g (50%) of the title compound, m.p. 78–81° C.

$^1$H-NMR (CDCl$_3$), δ(ppm): 4.38–4.19 m (2H), 3.99–3.89 m (2H), 1.45 s (CH$_3$), 1.42 s (CH$_3$), 1.22 s (t-Bu), 1.19 s (CH$_3$).

B) 3,3,5-trimethyl-5-pivaloyloxymethylmorpholin-2-on-4-oxyl

A solution of 21.5 g (0.087 mol) of m-chloroperbenzoic acid (70%) in 50 ml of ethyl acetate is added dropwise, with stirring, to a solution of 14.9 g (0.058 mol) of 3,3,5-trimethyl-5-pivaloyloxymethylmorpholin-2-one in 80 ml of ethyl acetate at 10° C. The reaction mixture is stirred for another 2.5 hours at room temperature, washed with 3×120 ml of 1 M NaHCO$_3$ and water and is then dried over MgSO$_4$ and concentrated by evaporation in a rotary evaporator. The residue is recrystallised from acetonitrile.

This gives 10.5 g (66%) of compound (214), m.p. ~97° C.

Analysis calculated for C$_{13}$H$_{22}$NO$_5$: C 57.34%, H 8.14%, N 5.14%; found C 57.20%, H 8.06%, N 4.96%.

Example B12

4-(dimethylcyanomethyloxy)-3,3,5-trimethyl-5-pivaloyloxymethylmorpholin-2-one (215)

3.35 g (0.012 mol) of 3,3,5-trimethyl-5-pivaloyloxymethylmorpholin-2-on-4-oxyl and 1.5 g (0.009 mol) of azobisisobutyronitrile are refluxed for 3.5 hours under nitrogen in 15 ml of benzene. The benzene is then removed by distillation in a rotary evaporator and the residue is recrystallised from methanol.

This gives 2.67 g (65%) of compound (215), m.p. ~86° C.

Analysis calculated for C$_{17}$H$_{28}$N$_2$O$_5$: C 59.98%, H 8.29%, N 8.23%; found C 59.87%, H 8.12%, N 8.46%.

Example B13

3,3-diethyl-5-methyl-5-hydroxymethylmorpholin-2-one (216)

In analogy to Example B4 (compound 207), 3.55 g (9%) of compound (216) are obtained in the form of a colourless oil from 26.3 g (0.25 mol) of 2-amino-2-methyl-1,3-propanediol, 30 ml (0.375 mol) of chloroform, 265 ml (2.5 mol) of diethylketone and 50 g (1.25 mol) of sodium hydroxide.

$^1$H-NMR (CDCl$_3$), d(ppm): 4.42 d (1H), 4.07 d (1H), 3.40–3.30 m (2H), 2.0–1.5 m 2×(CH$_3$), 1.18 s (CH$_3$), 0.95 m 2×(CH$_3$).

Example B14

3,3-diethyl-5-methyl-5-pivaloyloxymethylmorpholin-2-one (217)

2.4 ml (0.017 mol) of triethylamine and then 2.15 g (0.018 mol) of pivaloyl chloride are added dropwise to a solution of 3.45 g (0.017 mol) of 3,3-diethyl-5-methyl-5-hydroxymethylmorpholin-2-one and 0.1 g of 4-dimethylaminopyridine in 20 ml dichloromethane at 15° C. After stirring for 20 hours, the precipitated triethylamine-hydrochloride is removed by filtration and the filtrate is washed with water, dried over MgSO$_4$ and concentrated by evaporation in a rotary evaporator. The residue is recrystallised from hexane. This gives 3.9 g (77%) of compound (217), m.p. 51–53° C.

Analysis calculated for C$_{15}$H$_{27}$NO$_4$: C 63.13%, H 9.54%, N 4.91%; found C 63.08%, H 9.56%, N 5.09%.

Example B15

3,3-diethyl-5-methyl-5-pivaloyloxymethylmorpholin-2-on-4-oxyl (218)

A solution of 6.2 g (0.025 mol) of m-chloroperbenzoic acid (70%) in 15 ml of ethyl acetate is added dropwise, with stirring, to a solution of 4.8 g (0.017 mol) of 3,3-diethyl-5-methyl-5-pivaloyloxymethylmorpholin-2-one in 25 ml of ethyl acetate at 10° C. The reaction mixture is stirred for another 24 hours at room temperature and is then washed with 1 M NaHCO$_3$ and water, dried over MgSO$_4$ and then concentrated by evaporation in a rotary evaporator. The residue is recrystallised from acetonitrile.

This gives 2.6 g (52%) of compound (218), m.p. 69–72° C.

Analysis calculated for C$_{15}$H$_{26}$NO$_5$: C 59.98%, H 8.72%, N 4.66%; found C 59.91%, H 8.53%, N 4.46%.

Example B16

4-(α-methylbenzyloxy)-3,3-diethyl-5-methyl-5-pivaloyloxymethylmorpholin-2-one (219)

In analogy to Example B10 (compound 213), 3.14 g (93%) of compound (219) are obtained in the form of a colourless oil from 2.5 g (0.008 mol) of 3,3-diethyl-5-methyl-5-pivaloyloxymethylmorpholin-2-on-4-oxyl, 6.45 ml (0.033 mol) of di-tert-butylperoxide and 200 ml of ethylbenzene.

$^1$H-NMR (CDCl$_3$), δ(ppm): 7.46–7.20 m (5arH), 4.80–4.65 m (1H), 4.2–3.9 m 2×(CH$_2$), 2.3–1.6 m 2×(CH$_2$), 1.55 d (CH$_3$), 1.30 s (t-Bu), 0.90 m 2×(CH$_3$).

Example B17

3,3,5-triethyl-5-hydroxymethylmorpholin-2-one (220)

In analogy to Example B4 (compound 207), 0.5 g (0.9%) of compound (220) is obtained in the form of a colourless oil from 29.8 g (0.25 mol) of 2-amino-2-ethyl-1,3-propanediol, 30 ml (0.375 mol) of chloroform, 265 ml (2.5 mol) of diethylketone and 50 g (1.25 mol) of sodium hydroxide.

$^1$H-NMR (CDCl$_3$), δ(ppm): 4.37 d (1H), 4.18 d (1H), 3.45–3.35 m (2H), 1.9–1.4 m 3×(CH$_2$), 0.95 m 3×(CH$_3$).

Example B18

3,3,5-triethyl-5-pivaloyloxymethylmorpholin-2-one (221)

In analogy to Example B14 (compound (217), 8.45 g (75%) of compound (221), m.p. 37–41° C. (hexane), are obtained from 8.1 g (0.037 mol) of 3,3,5-triethyl-5-hydroxymethylmorpholin-2-one, 0.2 g of 4-dimethylaminopyridine, 5.3 ml (0.038 mol) of triethylamine and 5.15 ml (0.042 mol) of pivaloyl chloride.

Analysis calculated for C$_{16}$H$_{29}$NO$_4$: C 64.19%, H 9.76%, N 4.68%; found C 64.18%, H 9.78%, N 4.82%.

Example B19

3,3,5-triethyl-5-pivaloyloxymethylmorpholin-2-on-4-oxyl (222)

In analogy to Example B15 (compound (218), 8.0 g (98%) of compound (222) are obtained in the form of a red oil from 7.8 g (0.026 mol) of 3,3,5-triethyl-5-pivaloyloxymethylmorpholin-2-one and 9.6 g (0.039 mol) of m-chloroperbenzoic acid (70%).

Analysis calculated for $C_{16}H_{28}NO_5$: C 61.12%, H 8.98%, N-4.46%; found C 60.95%, H 9.07%, N 4.35%.

Example B20

4-(α-methylbenzyloxy)-3,3,5-triethyl-5-pivaloyloxymethylmorpholin-2-one (223)

In analogy to Example B10 (compound 213), 7.65 g (91%) of compound (223) are obtained in the form of a colourless oil from 6.3 g (0.020 mol) of 3,3,5-triethyl-5-pivaloyloxymethylmorpholin-2-on-4-oxyl, 15.5 ml (0.080 mol) of di-tert-butylperoxide and 200 ml of ethylbenzene.

Analysis calculated for $C_{24}H_{37}NO_5$: C 68.71%, H 8.89%, N 3.34%; found C 68.61%, H 8.84%, N 3.21%.

Example B21

1-isopropyl-3-ethyl-3,5,5-trimethylpiperazin-2-one (229)

40 g (1 mol) of finely ground NaOH are added, with stirring, to a solution of 24.6 g (0.189 mol) of N-1-isopropyl-2-methylpropane-1,2-diamine (prepared in accordance with M. Senkus.: J. Am. Chem. Soc. 68, 10 (1946)) and 25 ml (0.3 mol) of chloroform in 250 ml (2.77 mol) of methyl ethyl ketone at 10° C. The reaction mixture is stirred for 16 hours at room temperature and is then filtered. The filtrate, concentrated by evaporation in a rotary evaporator, is chromatographed over silica gel with hexane/ethyl acetate (3:2). The pure fractions are concentrated by evaporation, giving 13.7 g (33%) of compound (229) in the form of a colourless oil.

$^1$H-NMR (CDCl$_3$), δ(ppm): 4.96 m (1H), 3.0 m (CH$_2$), 1.9–1.4 m (CH$_2$), 1.35 s (CH$_3$), 1.18 s 2×(CH$_3$), 1.07 d 2×(CH$_3$), 0.88 t (CH$_3$).

Example B22

1-isopropyl-3-ethyl-3,5,5-trimethylpiperazin-2-on-4-oxyl (230)

0.4 g of sodium tungstate, 2 g of sodium carbonate and then, at 10° C., 27.5 ml of hydrogen peroxide (35%, in water) are added to a solution of 13.7 g (0.064 mol) of 1-isopropyl-3-ethyl-3,5,5-trimethylpiperazin-2-one in 50 ml of methanol. The reaction mixture is stirred for 40 hours at room temperature and is then diluted with 100 ml of saturated NaCl solution and extracted with 5×50 ml of methyl-tert-butyl ether. The extracts are dried over MgSO$_4$, concentrated by evaporation and chromatographed over silica gel with hexane/ethyl acetate (3:1). The pure fractions are concentrated by evaporation, giving 9.4 g (64%) of compound (230) in the form of a red oil.

Analysis calculated for $C_{12}H_{23}N_2O_2$: C 63.40%, H 10.20%, N 12.32%; found C 63.34%, H 10.36%, N 11.81%.

Example B23

4-(dimethylcyanomethyloxy)-1-isopropyl-3-ethyl-3,5,5-trimethylpiperazin-2-one (231)

4.55 g (0.02 mol) of 1-isopropyl-3-ethyl-3,5,5-tetramethylpiperazine-2-on-4-oxyl and 4.93 g (0.03 mol) of azobisisobutyronitrile are refluxed for 2 hours under nitrogen in 20 ml of benzene. The benzene is then removed by distillation in a rotary evaporator and the residue is chromatographed over silica gel with hexane/ethyl acetate (9:1). 2.25 g (38%) of compound (231) are obtained in the form of a colourless solid, m.p. 106–108° C. Analysis calculated for $C_{16}H_{29}N_3O_2$: C 65.05%, H 9.89%, N 14.22%; found C 65.10%, H 9.83%, N 14.27%.

Example B24

4-(α-methylbenzyloxy)-1-isopropyl-3-ethyl-3,5,5-trimethylpiperazin-2-one (232)

In analogy to Example B3, compound (206), 3.41 g (0.015 mol) of 1-isopropyl-3-ethyl-3,5,5-trimethylpiperazin-2-on-4-oxyl are reacted with 11 ml (0.06 mol) of t-butylperoxide and ethylbenzene as solvent, resulting in 4.55 g (91%) of the desired compound in the form of a colourless oil.

Elemental analysis calculated for $C_{20}H_{32}N_2O_2$: C 72.25%; H 9.70%; N 8.43%. Found: C 71.80%; H 9.86%; N 8.24%.

Example B25

1-isopropyl-3,3-diethyl-5,5-dimethylpiperazin-2-one (233)

In analogy to Example B21, compound (229), 16.4 g (36%) of compound (233) are obtained in the form of a colourless oil from 26.1 g (0.2 mol) of N-1-isopropyl-2-methylpropane-1,2-diamine, 25 ml (0.3 mol) of chloroform, 265 ml (2.5 mol) of diethylketone and 40 g (1 mol) of NaOH.

$^1$H-NMR (CDCl$_3$), δ(ppm): 4.98 m (1H), 3.0 m (CH$_2$), 1.8–1.4 m 2×(CH$_2$), 1.16 s 2×(CH$_3$), 1.70 d 2×(CH$_3$), 0.88 t 2×(CH$_3$).

Example B26

1-isopropyl-3,3-diethyl-5,5-dimethylpiperazin-2-on-4-oxyl (234)

In analogy to Example B22, compound (230), 11.5 g (70%) of compound (234) are obtained in the form of a red oil from 15.4 g (0.07 mol) of 1-isopropyl-3,3-diethyl-5,5-dimethylpiperazin-2-one, 0.4 g of sodium tungstate, 2 g of sodium carbonate and 25 ml of hydrogen peroxide (35%, in water).

Analysis calculated for $C_{13}H_{25}N_2O_2$: C 64.69%, H 10.44%, N 11.61%; found C 64.67%, H 10.44%, N 11.47%.

Example B27

4-(dimethylcyanomethyloxy)-1-isopropyl-3,3-diethyl-5,5-dimethylpiperazin-2-one (235)

In analogy to Example B23, compound (231), 1.64 g (53%) of compound (235) are obtained in the form of a colourless solid, m.p. 84–89° C., from 2.41 g,(0.01 mol) of 1-isopropyl-3,3-diethyl-5,5-dimethyl-piperazin-2-on-4-oxyl and 2.46 g (0.015 mol) of azobis-isobutyronitrile.

Analysis calculated for $C_{17}H_{31}N_3O_2$: C 65.98%, H 10.10%, N 13.58%; found C 65.73%, H 10.04%, N 13.61%.

Example B28

1-isopropyl-4-(α-methylbenzyloxy)-3,3-diethyl-5,5-dimethylpiperazin-2-one (236)

In analogy to Example B10 (compound 213), 6.2 g (89%) of compound (236) are obtained in the form of a colourless oil from 4.8 g (0.020 mol) of 1-isopropyl-3,3-diethyl-5,5-dimethylpiperazin-2-on-4-oxyl, 15.5 ml (0.080 mol) of di-tert-butylperoxide and 250 ml of ethylbenzene.

Analysis calculated for $C_{21}H_{34}N_2O_2$: C 72.79%, H 9.89%, N 8.08%; found C 72.61%, H 9.89%, N 8.15%.

Example B29

1-t-butyl-3,3-diethyl-5,5-dimethylpiperazin-2-one (237)

In analogy to Example B21, compound (229), 44.2 g (66%) of compound (237) are obtained in the form of a colourless oil from 39.7 g (0.275 mol) of 1,1-dimethyl-2-t-butylaminopropylamine (prepared in accordance with G. Smith et al.: J. Chem. Soc. 886 (1962)), 33.5 ml (0.412 mol) of chloroform, 360 ml (3.4 mol) of diethylketone and 55 g (1.375 mol) of NaOH.

$^1$H-NMR (CDCl$_3$), δ(ppm): 3.16 s (CH$_2$), 1.7–1.5 m 2×(CH$_2$), 1.42 s (t-Bu), 1.15 s 2×(CH$_3$), 0.89 t 2×(CH$_3$).

Example B30

1-t-butyl-3,3-diethyl-5,5-dimethylpiperazin-2-on-4-oxyl (238)

In analogy to Example B22, compound (230), 41 g (99%) of compound (238) are obtained in the form of a red oil from 38.9 g (0.162 mol) of 1-t-butyl-3,3-diethyl-5,5-dimethylpiperazin-2-one, 1 g of sodium tungstate, 5 g of sodium carbonate and 56 ml of hydrogen peroxide (35%, in water).

Analysis calculated for $C_{14}H_{27}N_2O_2$: C 65.84%, H 10.66%, N 10.97%; found C 65.59%, H 10.87%, N 10.75%.

Example B31

1-t-butyl-4-(α-methylbenzyloxy)-3,3-diethyl-5,5-dimethylpiperazin-2-one (239)

In analogy to Example B10 (compound 213), 6.6 g (91%) of compound (239) are obtained in the form of a colourless oil from 5.11 g (0.020 mol) of 1-t-butyl-3,3-diethyl-5,5-dimethylpiperazin-2-on-4-oxyl, 15.5 ml (0.080 mol) of di-tert-butylperoxide and 300 ml of ethylbenzene.

Analysis calculated for $C_{22}H_{36}N_2O_2$: C 73.29%, H 10.06%, N 7.77%; found C 73.41%, H 10.19%, N 7.75%.

Example B32

4-(dimethylcyanomethyloxy)-1-t-butyl-3,3-diethyl-5,5-dimethylpipe-razin-2-one (240)

In analogy to Example B23, compound (231), 8.7 g (67%) of compound (240) are obtained in the form of a colourless solid, m.p. 68–71° C., from 10.2 g (0.04 mol) of 1-t-butyl-3,3-diethyl-5,5-dimethyl-piperazin-2-on-4-oxyl and 4.9 g (0.03 mol) of azobisisobutyronitrile. Analysis calculated for $C_{18}H_{33}N_3O_2$: C 66.84%, H 10.28%, N 12.99%; found C 66.72%, H 10.08%, N 13.03%.

Example B33

3,3-diethyl-5,5,6,6-tetramethylpiperazin-2-one (241)

In analogy to Example B21, compound (229), 1.85 g (9%) of compound (241) are obtained in the form of an amorphous solid from 18.9 g (0.1 mol) of 1,1,2,2-tetramethyl-1,2-ethanediamine dihydrochloride (prepared in accordance with G. Smith et al.: J. Chem. Soc. 886 (1962)), 12.5 ml (0.15 mol) of chloroform, 235 ml (1.25 mol) of diethylketone and 20 g (0.5 mol) of NaOH.

$^1$H-NMR (CDCl$_3$), δ(ppm): 5.56 s (NH), 1.69 q 2×(CH$_2$), 1.21 s 2×(CH$_3$), 1.15 s2×(CH$_3$), 0.95 t 2×(CH$_3$).

Example B34

3,3-diethyl-5,5,6,6-tetramethylpiperazin-2-on-4-oxyl (242)

In analogy to Example B22, compound (230), 0.35 g (19%) of compound (242) are obtained in the form of a red solid, m.p. ~135° C., from 1.7 g (0.008 mol) of 3,3-diethyl-5,5,6,6-tetramethylpiperazin-2-one, 0.25 g of sodium tungstate, 0.8 g of sodium carbonate and 4.5 ml of hydrogen peroxide (35%, in water).

Example B35

4-(dimethylcyanomethyloxy)-3,3-diethyl-5,5,6,6-tetramethylpiperazin-2-one (243)

In analogy to Example B23, compound (231), 0.29 g (65%) of compound (243) are obtained in the form of a colourless solid, m.p. 140–145° C., from 0.35 g (0.0015 mol) of 3,3-diethyl-5,5,6,6-tetramethylpiperazin-2-on-4-oxyl and 0.25 g (0.0015 mol) of azobisisobutyronitrile.

$^1$H-NMR (CDCl$_3$), δ(ppm): 5.88 s (NH), 2.3–1.8 m 2×(CH$_2$),1.73 s (CH$_3$), 1.72 s (CH$_3$), 1.43 s (CH$_3$), 1.30 s (CH$_3$), 1.18 s (CH$_3$), 1.17 s (CH$_3$), 1.05 m 2×(CH$_3$).

Example B36

1-benzyl-3,3-diethyl-5,5-dimethylpiperazin-2-one (244)

In analogy to Example B21, compound (229), 46.2 g (61%) of compound (244) are obtained in the form of a colourless oil from 49 g (0.275 mol) of N-1-benzyl-2-methylpropane-1,2-diamine (prepared in accordance with M. Senkus.: J. Am. Chem. Soc. 68, 10 (1946)), 25 ml (0.3 mol) of chloroform, 360 ml (3.4 mol) of diethylketone and 55 g (1.375 mol) of NaOH.

$^1$H-NMR (CDCl$_3$), δ(ppm): 7.28 m (C$_6$H$_5$), 4.60 s (CH$_2$), 3.03 s (CH$_2$), 1.8–1.6 m 2×(CH$_2$), 1.07 s 2×(CH$_3$), 0.86 t 2×(CH$_3$).

Example B37

1-benzyl-3,3-diethyl-5,5-dimethylpiperazin-2-on-4-oxyl (245)

In analogy to Example B22, compound (230), 41.9 g (96%) of compound (245) are obtained in the form of a red oil from 41 g (0.15 mol) of 1-benzyl-3,3-diethyl-5,5-dimethyl-piperazin-2-one, 1 g of sodium tungstate, 5 g of sodium carbonate and 52 ml of hydrogen peroxide (35%, in water).

Analysis calculated for $C_{17}H_{25}N_2O_2$: C 70.56%, H 8.71%, N 9.68%; found C 70.06%, H 8.34%, N 9.44%.

Example B38

1-(2-hydroxyethyl)-3,3-diethyl-5,5-dimethylpiperazin-2-one (246)

In analogy to Example B21, compound (229), 32.6 g (48%) of compound (246) are obtained in the form of a colourless oil from 39.7 g (0.3 mol) of N-(2-hydroxyethyl)-2-methyl-propane-1,2-diamine, 37 ml (0.45 mol) of chloroform, 380 ml (3.6 mol) of diethylketone and, 60 g (1.5 mol) of NaOH.

$^1$H-NMR (CDCl$_3$), δ(ppm): 3.78 t (CH$_2$), 3.55 t (CH$_2$), 1.8–1.6 m 2×(CH$_2$), 1.20 s 2×(CH$_3$), 0.88 t 2×(CH$_3$).

Example B39

1-t-Butyl-3-ethyl-3,5,5-trimethyl-piperazin-2-on (247)

In analogy to Example B21, 1,1-dimethyl-2-t-butylaminoethylamin, methylethylketon, chloroform and NaOH are reacted to give the raw title compound (99%) as an yellow oil.

$^1$H-NMR (CDCl$_3$), δ(ppm): 3.17d (CH$_2$), 1.8–1.6 m (CH$_2$), 1.42 s (t-Bu), 1.34 s, 1.20 s, 1.18 s 3×(CH3), 0.89 t (CH$_3$).

Example B40

1-t-Butyl-3-ethyl-3,5,5-trimethyl-piperazin-2-on-4-oxyl (248)

45.3 g (0.2 Mol) of raw compound (247) are dissolved in 450 ml of ethylacetate and 51.1 ml (0.3 Mol) of peracetic acid (39% in acetic acid) are added to the stirred solution under cooling within 20 minutes. The solution is stirred for another 2.5 hours, then diluted with 100 ml of hexane and washed with NaHCO$_3$ solution till neutral. The title compound (248) is obtained after evaporation of hexane, chromatography of the residue on Silica gel with hexane-EtOAc (5:1) and crystallization from pentane. Yield 23.7 g (49%) of red crystals, m.p. 50–53° C.

Elemental analysis, for C$_{13}$H$_{25}$N$_2$O$_2$ calculated: C 64.69%, H 10.44%, N 11.61%; found: C 64.58%, H 10.51%, N 11.61%.

Example B41

1-t-Butyl-4-(α-methylbenzyloxy)-3-ethyl-3,5,5-trimethyl-piperazin-2-on (249)

In analogy to Example B10, the compound (249) is transformed into the title compound as a colorless oil.

$^1$H-NMR (CDCl$_3$), δ(ppm): 7.36–7.25 m (5 ArH), 4.76–4.65 m (1H), 3.17–2.82 m (CH$_2$), 1.89–0.53 m (26H).

Example B42

1-t-Butyl-3,5-diethyl-3,5-dimethyl-piperazin-2-on (250)

A) 1-Ethyl-1-methyl-2-t-butylaminoethylamin

This amine has been prepared from 2-nitrobutane following the method of G. Smith et al. (J. Chem. Soc. 886 (1962)).

B) In analogy to Example B23, 1-ethyl-1-methyl-2-t-butylaminoethylamin, methylethylketon, chloroform and NaOH are reacted to give the raw title compound (100%) as an yellow oil.

$^1$H-NMR (CDCl$_3$), δ(ppm): 3.25–3.08 m (CH$_2$), 1.7–0.84 m (25H).

Example B43

1-t-Butyl-3,5-diethyl-3,5-dimethyl-piperazin-2-on-4-oxyl (251)

In analogy to Example B40, the compound (250) is transformed into the title compound as a red oil.

Elemental analysis, for C$_{14}$H$_{27}$N$_2$O$_2$ calculated: C 65.84%, H 10.66%, N 10.97%; found: C 65.22%, H 10.63%, N 10.97%.

Example B44

1-t-Butyl-4-(α-methylbenzyloxy)-3,5-diethyl-3,5-dimethyl-piperazin-2-on (252)

In analogy to Example B10, the compound (251) is transformed into the title compound as a colorless oil.

$^1$H-NMR (CDCl$_3$), δ(ppm): 7.36–7.23 m (5 ArH), 4.75–4.66 m (1H), 3.20–2.84 m (CH$_2$), 1.93–0.59 m (28H).

Example B45

1-t-Butyl-5,5-diethyl-3,3-dimethyl-piperazin-2-on (253)

A) 1,1-Diethyl-2-t-butylaminoethylamin

This amine has been prepared from 3-nitropentane following the method of G. Smith et al. (J. Chem. Soc. 886 (1962)).

B) In analogy to Example B21, 1,1-diethyl-2-t-butylaminoethylamin, aceton, chloroform and NaOH are reacted to give the title compound (77%) as an yellow oil.

$^1$H-NMR (CDCl$_3$), δ(ppm): 3.21 s (CH$_2$), 1.51–1.37 m, 2×(CH$_2$), 1.43 s (t-Bu), 1.36 s, 2×(CH$_3$), 0.85 t, 2×(CH$_3$).

Example B46

1-t-Butyl-5,5-diethyl-3,3-dimethyl-piperazin-2-on-4-oxyl (254)

In analogy to Example B22, the compound (253) is transformed into the title compound (89%) as a red crystals, m.p. 53–55° C.

Elemental analysis, for C$_{14}$H$_{27}$N$_2$O$_2$ calculated: C 65.84%, H 10.66%, N 10.97%; found: C 65.98%, H 10.70%, N 11.09%.

Example B47

1-t-Butyl-4-(dimethylcyanomethyloxy)-5,5-diethyl-3,3-dimethylpiperazin-2-on (255)

In analogy to Example B23, the compound (254) is transformed into the title compound (89%) as a colorless oil.

$^1$H-NMR (CDCl$_3$), δ(ppm): 3.27–3.03 m (CH$_2$), 1.84–1.76 m, (CH$_2$), 1.66 s, 1.64 s, 2×(CH$_3$), 1.50 s, 1.49 s, 2×(CH$_3$), 1.46–1.41 m, (CH$_2$), 1.39 s (t-Bu), 0.97–0.91 m (CH$_3$).

Example B48

1-t-Butyl-3,5,5-triethyl-3-methyl-piperazin-2-on (256)

In analogy to Example B21, 1,1-diethyl-2-t-butylaminoethylamin, methylethylketon, chloroform and NaOH are reacted to give the title compound (64%) as an yellow oil.

$^1$H-NMR (CDCl$_3$), δ(ppm): 3.25–3.16 m (CH$_2$), 2.05–1.38 m, 3×(CH$_2$), 1.43 (CH$_3$), 0.93–0.83 m, 3×(CH$_3$).

Example B49

1-t-Butyl-3,5,5-triethyl-3-methyl-piperazin-2-on-4-oxyl (257)

In analogy to Example B22, the compound (256) is transformed into the title compound (88%) as a red crystals, m.p. 57–60° C.

Elemental analysis, for $C_{15}H_{29}N_2O_2$ calculated: C 65.84%, H 10.66%, N 10.97%; found: C 66.87%, H 10.85%, N 10.40%.

Example B50

1-t-Butyl-4-(dimethylcyanomethyloxy)-3,5,5-triethyl-3-methyl-piperazin-2-on (258)

In analogy to Example B23, the compound (257) is transformed into the title compound (83%) as colorless crystals, m.p. 78–80° C.

$^1$H-NMR (CDCl$_3$), δ(ppm): 3.21–3.04 m (CH$_2$), 2.04–1.80 m, 2×(CH$_2$), 1.66 s, 1.64 s, 1.45 s, 3×(CH$_3$), 1.41 s (t-Bu), 1.0–0.92 m (CH$_3$).

Example B51

1-t-Butyl-4-benzyloxy-3,5,5-triethyl-3-methyl-piperazin-2-on (259)

In analogy to Example B10 and using toluene instead of ethylbenzene, the compound (257) is transformed into the title compound as a colorless oil.

$^1$H-NMR (CDCl$_3$), δ(ppm): 7.39–7.28 m (5 ArH), 4.85–4.76 m (CH$_2$), 3.13–3.08 m (CH$_2$), 1.92–0.86 m (27H).

Example B52

1-t-Butyl-4-(α-methylbenzyloxy)-3,5,5-triethyl-3-methyl-piperazin-2-on (260)

In analogy to Example B10, the compound (257) is transformed into the title compound as a colorless solid, m.p. 76–79° C.

Elemental analysis, for $C_{28}H_{38}N_2O_2$ calculated: C 73.75%, H 10.23%, N 7.48%; found: C 73.51%, H 9.68%, N 7.12%.

Example B53

1-t-Butyl-3,3,5-triethyl-5-methyl-piperazin-2-on (261)

In analogy to Example B21, 1-ethyl-1-methyl-2-t-butylaminoethylamin, diethylketon, chloroform and NaOH are reacted to give the raw title compound (71%) as an yellow oil.

$^1$H-NMR (CDCl$_3$), δ(ppm): 3.18–3.06 m (CH$_2$), 1.60–0.82 m (27H).

Example B54

1-t-Butyl-3,3,5-triethyl-5-methyl-piperazin-2-on-4-oxyl (262)

In analogy to Example B40, the compound (261) is transformed into the title compound as a red oil.

Example B55

1-t-Butyl-4-(α-methylbenzyloxy)-3,3,5-triethyl-5-methyl-piperazin-2-on (263)

In analogy to Example B10, the compound (262) is transformed into the title compound as a colorless oil.

$^1$H-NMR (CDCl$_3$), δ(ppm): 7.37–7.28 m (5 ArH), 4.75–4.69 m (1H), 3.22–2.90 m (CH$_2$), 2.14–0.63 m (30H).

Example B56

1-t-Butyl-3,3,5,5-tetraethyl-piperazin-2-on (264)

In analogy to Example B21, 1,1-diethyl-2-t-butylaminoethylamin, diethylketon, chloroform and NaOH are reacted to give the title compound (52%) as a yellow oil.

Elemental analysis, for $C_{16}H_{32}N_2O$ calculated: C 71.58%, H 12.02%, N 10.44%; found: C 71.38%, H 12.05%, N 10.13%.

Example B57

1-t-Butyl-3,3,5,5-tetraethyl-piperazin-2-on-4-oxyl (265)

In analogy to Example B40, the compound (264) is transformed into the title compound as red crystals, m.p. 34–37° C.

Elemental analysis, for $C_{16}H_{31}N_2O_2$ calculated: C 67.80%, H 11.02%, N 9.88%; found: C 67.78%, H 11.06%, N 9.88%.

Example B58

1-t-Butyl-4-benzyloxy-3,3,5,5-tetraethyl-piperazin-2-on (266)

In analogy to Example B10 and using toluene instead of ethylbenzene, the compound (265) is transformed into the title compound as colorless crystals, m.p. 83–85° C.

Elemental analysis, for $C_{23}H_{38}N_2O_2$ calculated: C 73.75%, H 10.23%, N 7.48%; found: C 74.33%, H 10.26%, N 7.41%.

Example B59

1-t-Butyl-4-(α-methylbenzyloxy)-3,3,5,5-tetraethyl-piperazin-2-on (267)

In analogy to Example B10, the compound (265) is transformed into the title compound as colorless crystals, m.p. 85–90° C.

Elemental analysis, for $C_{24}H_{40}N_2O_2$ calculated: C 74.18%, H 10.38%, N 7.21%; found: C 74.40%, H 10.44%, N 7.08%.

Example B60

1-t-Butyl-4-(dimethylcyanomethyloxy)-3,3,5,5-tetraethyl-piperazin-2-on (268)

In analogy to Example B23, the compound (265) is transformed into the title compound as colorless crystals, m.p. 45–52° C.

Elemental analysis, for $C_{20}H_{37}N_3O_2$ calculated: C 68.33%, H 10.61%, N 11.95%; found: C 68.33%, H 10.67%, N 11.84%.

Example B61

1-t-Butyl-3,3-cyclohexyliden-5,5-diethyl-piperazin-2-on (269)

In analogy to Example B21, 1,1-diethyl-2-t-butylaminoethylamin, cyclohexanon, chloroform and NaOH are reacted to give the title compound as a yellow oil.

$^1$H-NMR (CDCl$_3$), δ(ppm): 3.16 s (CH$_2$), 2.26–0.82 m (20H), 1.41 s (t-Bu).

Example B62

1-t-Butyl-3,3-cyclohexyliden-5,5-diethyl-piperazin-2-on-4-oxyl (270)

In analogy to Example B22, the compound (269) is transformed into the title compound as a red oil.

Example B63

1-t-Butyl-3,3-cyclohexyliden-4-(α-methylbenzyloxy)-5,5-diethyl-piperazin-2-on-4-oxyl (271)

In analogy to Example B10, the compound (270) is transformed into the title compound as colorless crystals, m.p. 93–96° C.

Elemental analysis, for $C_{25}H_{40}N_2O_2$ calculated: C 74.96%, H 10.06%, N 6.99%; found: C 74.79%, H 9.69%, N 6.66%.

Example B64

1-t-Butyl-3,3-dipropyl-5,5-dimethyl-piperazin-2-on (272)

In analogy to Example B21, 1,1-dimethyl-2-t-butylaminoethylamin, dipropylketon, chloroform and NaOH are reacted to give the title compound as a yellow oil.

$^1$H-NMR (CDCl$_3$), δ(ppm): 3.22 s (CH$_2$), 1.7–0.8 m (20H), 1.41 s (t-Bu).

Example B65

1-t-Butyl-3,3-dipropyl-5,5-dimethyl-piperazin-2-on-4-oxyl (273)

In analogy to Example B10, the compound (272) is transformed into the title compound as colorless crystals, m.p. 67–70° C.

Elemental analysis, for $C_{16}H_{31}N_2O_2$ calculated: C 67.80%, H 11.02%, N 9.88%; found: C 67.69%, H 10.77%, N 9.87%.

Example B66

1-t-Butyl-4-(dimethylcyanomethyloxy)-3,3-dipropyl-5,5-dimethyl-piperazin-2-on (274)

In analogy to Example B23, the compound (273) is transformed into the title compound as colorless crystals, m.p. 85–87° C.

Elemental analysis, for $C_{20}H_{37}N_3O_2$ calculated: C 68.34%, H 10.61%, N 11.95%; found: C 68.32%, H 10.50%, N 12.05%.

Example B67

1-t-Butyl-3,3-dipropyl-5,5-diethyl-piperazin-2-on (275)

In analogy to Example B21, 1,1-diethyl-2-t-butylaminoethylamin, dipropylketon, chloroform and NaOH are reacted to give the title compound as a yellow oil.

$^1$H-NMR (CDCl$_3$), δ(ppm): 3.14 s (CH$_2$), 1.7–0.8 m (24H), 1.41 s (t-Bu).

Example B68

1-t-Butyl-3,3-dipropyl-5,5-diethyl-piperazin-2-on-4-oxyl (276)

In analogy to Example B22, the compound (275) is transformed into the title compound as red crystals, m.p. 62–64° C.

Elemental analysis, for $C_{18}H_{35}N_2O_2$ calculated: C 69.41%, H 11.33%, N 8.99%; found: C 68.37%, H 11.50%, N 9.04%.

Example B69

1-t-Butyl-3,3-dipropyl-4-(α-methylbenzyloxy)-5,5-diethyl-piperazin-2-on (277)

In analogy to Example B10, the compound (276) is transformed into the title compound as a colorless oil.

$^1$H-NMR (CDCl$_3$), δ(ppm): 7.37–7.22 m (5 ArH), 4.75–4.64 m (1H), 3.21–2.96 m (CH$_2$), 2.1–0.62 m (36H).

Example B70

1-t-Butyl-3,3-dibutyl-5,5-dimethyl-piperazin-2-on (278)

In analogy to Example B21, 1,1-dimethyl-2-t-butylaminoethylamin, dibutylketon, chloroform and NaOH are reacted to give the title compound as a yellow oil.

$^1$H-NMR (CDCl$_3$), δ(ppm): 3.16 s (CH$_2$), 1.7–0.8 m (24H), 1.42 s (t-Bu).

Example B71

1-t-Butyl-3,3-dibutyl-5,5-dimethyl-piperazin-2-on-4-oxyl (279)

In analogy to Example B22, the compound (278) is transformed into the title compound as red crystals, m.p. 36–48° C.

Elemental analysis, for $C_{18}H_{35}N_2O_2$ calculated: C 69.41%, H 11.33%, N 8.99%; found: C 69.35%, H 11.09%, N 9.04%.

Example B72

1-t-Butyl-3,3-dibutyl-4-(dimethylcyanomethyloxy)-5,5-dimethyl-piperazin-2-on (280)

In analogy to Example B23, the compound (279) is transformed into the title compound as colorless crystals, m.p. 68–74° C.

$^1$H-NMR (CDCl$_3$), δ(ppm): 3.18–3.04 m (CH$_2$), 2.1–0.8 m (30H), 1.40 s (t-Bu).

Example B73

1-t-Octyl-3,3-diethyl-5,5-dimethyl-piperazin-2-on (281)

In analogy to Example B21, 1,1-dimethyl-2-t-octylaminoethylamin, diethylketon, chloroform and NaOH are reacted to give the title compound as a yellow oil.

$^1$H-NMR (CDCl$_3$), δ(ppm): 3.17 s (CH$_2$), 1.9–0.8 m (31H).

Example B74

1-t-Octyl-3,3-diethyl-5,5-dimethyl-piperazin-2-on-4-oxyl (282)

In analogy to Example B22, the compound (281) is transformed into the title compound as red crystals, m.p. 54–56° C.

Elemental analysis, for $C_{18}H_{35}N_2O_2$ calculated: C 69.41%, H 11.33%, N 8.99%; found: C 69.43%, H 11.39%, N 9.03%.

Example B75

1-t-Octyl-3,3-diethyl-4-(dimethylcyanomethyloxy)-5,5-dimethyl-piperazin-2-on (283)

In analogy to Example B23, the compound (282) is transformed into the title compound as colorless crystals, m.p. 49–53° C.

Example B76

1-t-Octyl-3,3-diethyl-4-(α-methylbenzyloxy)-5,5-dimethyl-piperazin-2-on (284)

In analogy to Example B10, the compound (283) is transformed into the title compound as a colorless oil.

$^1$H-NMR (CDCl$_3$), δ(ppm): 7.49–7.38 m (5 ArH), 4.86–4.81 m (1H), 3.27–3.03 m (CH$_2$), 2.3–0.7 m (36H).

Example B77

1-(2-Hydroxyethyl)-3,3-diethyl-5,5-dimethyl-piperazin-2-on-4-oxyl (285)

In analogy to Example B22, the compound (246) is transformed into the title compound as a red oil.

Elemental analysis, for C$_{12}$H$_{23}$N$_2$O$_3$ calculated: C 59.23%, H 9.53%, N 11.51%; found: C 59.17%, H 9.52%, N 11.34%.

Example B78

1-(2-Hydroxyethyl)-3,3-diethyl-4-(dimethylcyanomethyloxy)-5,5-dimethylpiperazin-2-on (286)

In analogy to Example B23, the compound (285) is transformed into the title compound as colorless crystals, m.p. 80–82° C.

Elemental analysis, for C$_{16}$H$_{29}$N$_3$O$_3$ calculated: C 61.71%, H 9.39%, N 13.49%; found: C 61.69%, H 9.58%, N 13.39%.

Example B79

1-(1,1-Dimethyl-2-hydroxyethyl)-3,3-diethyl-5,5-dimethyl-piperazin-2-on (287)

In analogy to Example B21, 1,1-dimethyl-2-hydroxyethylamin, diethylketon, chloroform and NaOH are reacted to give the title compound as a yellow oil.

$^1$H-NMR (CDCl$_3$), δ(ppm): 3.73 s (CH$_2$), 3.15 s (CH$_2$), 1.7–0.8 m (22H).

Example B80

1-(1,1-Dimethyl-2-hydroxyethyl)-3,3-diethyl-5,5-dimethyl-piperazin-2-on-4-oxyl (288)

In analogy to Example B22, the compound (287) is transformed into the title compound as a red oil.

Elemental analysis, for C$_{14}$H$_{27}$N$_2$O$_3$ calculated: C 61.96%, H 10.03%, N 10.32%; found: C 61.96%, H 9.92%, N 10.27%.

Example B81

1-(1,1-Dimethyl-2-hydroxyethyl)-3,3-diethyl-4-(dimethylcyanomethyloxy)-5,5-dimethyl-piperazin-2-on (289)

In analogy to Example B23, the compound (288) is transformed into the title compound as colorless crystals, m.p. 58–66° C.

Elemental analysis, for C$_{18}$H$_{33}$N$_3$O$_3$ calculated: C 63.69%, H 9.80%, N 12.38%; found: C 63.79%, H 9.75%, N 12.37%.

Example B82

1-t-Butyl-3,3-diethyl-4-allyloxy-5,5-dimethyl-piperazin-2-on (290)

A) 1-t-Butyl-3,3-diethyl-4-hydroxy-5,5-dimethyl-piperazin-2-on 50.1 g (0.196 Mol) of the nitroxide (238) are hydrogenated in a methanolic solution at r.t. over Pt at 1 bar H$_2$ untill the hydrogen uptake stops. The catalyst is filtered off and the solvent is evaporated to give the crude title hydroxylamine.

B)

To a solution of 10.25 g (0.04 Mol) of the above hydroxylamine in 40 ml dimethylformamide are added 2.1 g (0.048 Mol) of NaH (60% in Oil). After 1 hour stirring, 5.81 g (0.048 Mol) of allylbromide are added and the mixture is stirred for another 3 h. The title compound (9.7 g, 82%) is obtained after dilution with water, extraction with methyl-t-butylether and chromatography on silicagel (hexane-EtOAc 2:1) as a colorless oil.

Elemental analysis, for C$_{17}$H$_{32}$N$_2$O$_2$ calculated: C 68.88%, H 10.88%, N 9.45%; found: C 68.99%, H 10.85%, N 9.50%.

Example B83

1-t-Butyl-3,3-diethyl-4-benzyloxy-5,5-di methyl-piperazin-2-on (291)

In analogy to Example B82 and using benzylbromide instead of allylbromide, the title compound is prepared as a colorless oil.

Elemental analysis, for C$_{21}$H$_{34}$N$_2$O$_2$ calculated: C 72.79%, H 9.89%, N 8.08%; found: C 72.63%, H 9.73%, N 8.05%.

Example B84

1-t-Butyl-3,3-diethyl-4-(α-cyanocyclohexyloxy)-5,5-dimethyl-piperazin-2-on (292)

2.8 g (0.011 Mol) of 1-t-butyl-3,3-diethyl-5,5-dimethyl-piperazin-2-on-4-oxyl (compound 238) and 2.0 g (0.0082 Mol) 1,1'-azobis-(cyclohexancarbonitril) are stirred at 100° C. in 12 ml of chlorobenzene under nitrogen for 11 h. Afterwards, the solvent is evaporated under vacuum and the semisolid residue is taken up in hexane. Filtration affords 2.2 g (55%) of the title compound as colorless crystals, m.p. 94–98° C.

Elemental analysis, for C$_{21}$H$_{37}$N$_3$O$_2$ calculated: C 69.38%, H 10.26%, N 11.56%; found: C 69.85%, H 9.89%, N 11.82%.

Example B85

1-t-Butyl-3,3-diethyl-4-α-methyl-4-acetylbenzyl)-5,5-dimethyl-piperazin-2-on (293)

In analogy to Example B10 and using 4-ethylacetophenon instead of ethylbenzene, the nitroxide (238) is transformed into the title compound as colorless crystals, m.p. 91–94° C.

Elemental analysis, for C$_{24}$H$_{38}$N$_2$O$_3$: calculated C 71.60%, H 9,51%, N 6.96%; found C %71.03, H 9.49%, N 6.90%.

Example B86

1-t-Butyl-3,3-diethyl-4-(α-methyl-4-acetoxybenzyl)-5,5-dimethylpiperazin-2-on (294)

In analogy to Example B10 and using 4-acetoxyethylbenzene instead of ethylbenzene, the nitrox-

---

Elemental analysis, for C$_{22}$H$_{41}$N$_3$O$_2$ calculated C 69.61%, H 10.89%, N 11.07%; found: C 69.60%, H 10.73%, N 11.22%.

ide (238) is transformed into the title compound as colorless crystals, m.p. 92–96° C.

Elemental analysis, for $C_{24}H_{38}N_2O_4$ calculated C 68.86%, H 9.15, N 6.69, found C 68.68%, 9.10%, N 6.46%.

Example B87

1-Phenyl-3,3-diethyl-5,5-dimethyl-piperazin-2-on (295)

In analogy to Example B21, 1,1-dimethyl-2-phenylaminoethylamin (prepared according H. G. Johnson, J. Am. Chem. Soc. 68,14 (1946)), diethylketon, chloroform and NaOH are reacted to give the title compound as colorless solid, m.p. 54–56° C.

$^1$H-NMR (CDCl$_3$), δ(ppm): 7.18–7.0 m (5 ArH), 3.31 s (CH$_2$),1.73–1.43 m (4H), 1.06 s 2×(CH$_3$), 0.75 t, 2×(CH3).

Example B88

1-Phenyl-3,3-diethyl-5,5-dimethyl-piperazin-2-on-4-oxyl (296)

In analogy to Example B40, the compound (295) is transformed into the title compound as red crystals, m.p. 71–76° C.

Elemental analysis, for $C_{16}H_{23}N_2O_2$ calculated: C 69.79%, H 8.42%, N 10.17%; found: C 70.04%, H 8.74%, N 10.19%.

Example B89

1-Phenyl-3,3-diethyl-4-(α-methylbenzyloxy)-5,5-dimethyl-piperazin-2-on (297)

In analogy to Example B10, the compound (296) is transformed into the title compound as colorless crystals, m.p. 78–81° C.

Elemental analysis, for $C_{24}H_{32}N_2O_2$ calculated: C 75.75%, H 8.48%, N 7.36%; found: C 75.83%, H 8.52%, N 7.50%.

Example B90

1-Methyl-3,3-diethyl-5,5-dimethyl-piperazin-2-on (298)

In analogy to Example B21, 1,1-Dimethyl-2-methylaminoethylamin (prepared according M. Senkus, J. Am. Chem. Soc. 68,10 (1946)), diethylketon, chloroform and NaOH are reacted to give the title compound as a colorless oil.

$^1$H-NMR (CDCl$_3$), δ(ppm): 3.14 s (CH$_2$), 2.80 s (CH$_3$), 1.8–0.7 m (10H), 1.18 s, 2×(CH$_3$),

Example B91

1-Methyl-3,3-diethyl-5,5-dimethyl-piperazin-2-on-4-oxyl (299)

In analogy to Example B40, the compound (298) is transformed into the title compound as red crystals, m.p. 72–76° C.

Example B92

1-Methyl-3,3-diethyl-4-(α-methylbenzyloxy)-5,5-dimethyl-piperazin-2-on (1200)

In analogy to Example B10, the compound (299) is transformed into the title compound as a colorless oil.

$^1$H-NMR (CDCl$_3$), δ(ppm): 7.28–7.19 m (5 ArH), 4.70–4.61m (1H), 3.27–2.6 m (CH$_2$), 2.83 s (CH$_3$), 2.2–0.5 m (19H).

Example B93

1-t-Butyl-3-isobutyl-3,5,5-trimethyl-piperazin-2-on (1201)

In analogy to Example B21, 1,1-dimethyl-2-t-butylaminoethylamin, methylisobutylketon, chloroform and NaOH are reacted to give the title compound as a colorless oil.

$^1$H-NMR (CDCl$_3$), δ(ppm): 3.17 s (CH$_2$),1.75–0.85 m (18H), 1.35 s, (t-Bu).

Example B94

1-t-Butyl-3-isobutyl-3,5,5-trimethyl-piperazin-2-on-4-oxyl (1202)

In analogy to Example B40, the compound (1201) is transformed into the title compound as red crystals, m.p. 32–37° C.

Example B95

1-t-Butyl-3-isobutyl-4-(α-methylbenzyloxy)-3,5,5-trimethyl-piperazin-2-on (1203)

In analogy to Example B10, the compound (1202) is transformed into the title compound as a colorless oil.

$^1$H-NMR (CDCl$_3$), δ(ppm): 7.38–7.26 m (5 ArH), 4.81–4.74m (1H), 3.21–2.87 m (CH$_2$), 2.1–0.65 m (21H), 1.40 s (t-Bu).

7-ring Compounds

Example C1

1-(dimethylcyanomethyloxy)-2,2,7,7-tetramethyl-[1,4]diazepan-5-one (301)

In analogy to Example B23, compound (231), 0.75 g (12%) of compound (301) are obtained in the form of a colourless solid, m.p. 130–134° C., from 4.6 g (0.025 mol) of 2,2,7,7-tetramethyl-[1,4]diazepan-5-on-1-oxyl (prepared in accordance to E. G. Rozantsev et al.: Izv. Akad. Nauk SSSR, Ser. Khim. 2114 (1980)) and 3.08 g (0.018 mol) of azobisisobutyronitrile. Analysis calculated for $C_{13}H_{23}N_3O_2$: C 61.63%, H 9.15%, N 16.59%; found C 61.41%, H 8.91%, N 16.73%.

Example C2

1-(α-methylbenzyloxy)-2,2,7,7-tetramethyl-[1,4]diazepan-5-one (302)

In analogy to Example B3, compound (206), 5.0 g (0.027 mol) of 2,2,7,7-tetramethyl-[1,4]diazepan-5-on-1-oxyl (prepared in accordance with E. G. Rozantsev et al.: Izv. Akad. Nauk SSSR, Ser. Khim. 2114 (1980)) are reacted with 20.9 ml (0.113 mol) of t-butylperoxide and ethylbenzene as solvent, resulting in 3.7 g (48%) of the desired compound in the form of a colourless solid, m.p. 125–127° C.

Analysis calculated for $C_{17}H_{26}N_2O_2$: C 70.31%, H 9.02%, N 9.65%; found C 69.99%, H 8.90%, N 9.56%.

Example C3

2,3,7-Trimethyl-2,7-diethyl-[1,4]diazepan-5-one-1-oxyl (303)

This nitroxide has been made according to DE 2621924.

Example C4

1-Benzyloxy-4-benzyl-2,3,7-trimethyl-2,7-diethyl-[1,4]diazepan-5-one (304)

A) 1-Hydroxy-2.3.7-trimethyl-2.7-diethyl-[1.4]diazepan-5-one

The solution of 4.55 g (0.02 Mol) of the nitroxide (303) in 20 ml of ethylacetate is during 3 h vigorously stirred with the solution of 7.9 g (0.04 Mol) of sodium ascorbate in 25 ml of water. The colorless organic layer is then separated, dried over $MgSO_4$ and evaporated in vacuum to give the title hydroxylamine as an amorphous, off white solid.

B)
8.0 g (0.035 Mol) of the preceding hydroxylamine are reacted as described in Example B83 with 10.4 ml (0.087 Mol) of benzylbromide and 3.8 g (0.0875 Mol) of NaH (55%) to afford 10.8 g (75%) of the title compound as a colorless oil.

$^1$H-NMR ($CDCl_3$), δ(ppm): 7.37–7.24 m (10 ArH), 5.03 s($CH_2$), 4.86–4.84 m ($CH_2$), 3.34–2.90 m ($CH_2$), 2.5–0.77 m (20H).

Example C5

1-Allyloxy-4-allyl-2,3,7-trimethyl-2,7-diethyl-[1,4]diazepan-5-one (305)

In analogy to example C4 but using allylbromide instead of benzylbromide, the title compound is prepared as a colorless oil.

Elemental analysis, for $C_{18}H_{32}N_2O_2$ calculated: C 70.09%, H 10.46%, N 9.08%; found: C 70.21%, H 10.72%, N 9.09%.

Example C6

2,3,4,7-Tetramethyl-2,7-diethyl-[1,4]diazepan-5-one-1-oxyl (306)

A solution of 2.25 g (0.009Mol) 2,3,7-trimethyl-2,7-diethyl-[1,4]diazepan-5-one-1-oxyl (303), 0.45 g tetrabutylammoniumhydrogensulfate and 9 ml methyliodide in 40 ml $CH_2Cl_2$ is stirred vigorously during 5 h with 64 g of 50% aqueous sodium hydroxide. The organic layer is then separated, washed with water and chromatographed on silica gel with hexane-EtOAc (9:1) to give 1.95 g (81%) of the title compound as a red oil.

Example C7

1-(α-Methylbenzyloxy)-2,3,4,7-tetramethyl-2,7-diethyl-[1,4]diazepan-5-one (307)

In analogy to Example B10, the compound (306) is transformed into the title compound as a colorless oil.

$^1$H-NMR ($CDCl_3$), δ(ppm): 7.34–7.08 m (5 ArH), 4.61–4.52 m (1H), 3.61 bs ($CH_3$), 2.3–0.45 m (25H).

Example C8

2,3,7-Trimethyl-2,7-diethyl-4-t-butyloxycarbonyl-[1,4]diazepan-5-one-1-oxyl (308)

To a solution of 13.1 g (0.06 Mol) of di-t-butyldicarbonate and 0.15 g 4-dimethylaminopyridine in 30 ml THF is slowly added the solution of 11.3 g (0.05 Mol) of the nitroxide (303) in 20 ml THF. The mixture is then stirred 16 h at r.t. and then evaporated. The residue is dissolved in $CH_2Cl_2$, washed with water, dried over $MgSO_4$ and evaporated again to give the title compound as a red oil.

Example C9

1-(α-Methylbenzyloxy)-2,3,7-trimethyl-2,7-diethyl-4-t-butyloxycarbo-nyl-[1,4]diazepan-5-one-(309)

In analogy to Example B10, the compound (308) is transformed into the title compound as a colorless oil.

$^1$H-NMR ($CDCl_3$), δ(ppm): 7.35–6.9 m (5 ArH), 4.58–4.51 m (1H), 2.3–0.45 m (25H), 1.29 s (t-Bu).

Example C10

1-(α-Methylbenzyloxy)-2,3,7-trimethyl-2,7-diethyl-[1,4]diazepan-5-one-(310)

To a solution of 2 g (0.0046 Mol) of the BOC-derivative (309) in 8 ml $CH_2Cl_2$ are added 2 ml of $CF_3COOH$ and the mixture is stirred 19 h at r.t. The title compound (1.1 g) is obtained after dilution with water, washing with $NaHCO_3$ solution, drying over $MgSO_4$ and evaporation as a colorless resin.

$^1$H-NMR ($CDCl_3$), δ(ppm): 7.35–6.9 m (5 ArH), 4.58–4.51 m (1H), 2.3–0.45 m (25H).

Example C11

4-Benzyl-2,3,7-trimethyl-2,7-diethyl-[1,4]diazepan-5-one-1-oxyl (311)

In analogy to Example C6 and using benzylchloride instead of methyliodide the compound (303) is transformed into the title compound as a red oil.

Example C12

1-Butyl-3,3,5,5,7-pentamethyl-[1,4]diazepan-2-one-4-oxyl (312)

In analogy to Example B40, the 1-butyl-3,3,5,5,7-pentamethyl-[1,4]diazepan-2-one (prepared as described by Pyong-nae Son, J. T. Lai.: J. Org. Chem. 46, 323 (1981)) is transformed into the title compound as a red oil.

Example C13

1-Butyl-4-(α-methylbenzyloxy)-3,3,5,5,7-pentamethyl-[1,4]diazepan-2-one (313)

In analogy to Example B10, the compound (312) is transformed into the title compound as a colorless oil.

$^1$H-NMR ($CDCl_3$), δ(ppm): 7.33–7.10 m (5 ArH), 4.66–4.55 m (1H), 4.20—4.10 m (1H), 3.13–3.01 m ($CH_2$), 1.6–0.5 m (27H).

Example C14

1-Butyl-3-ethyl-3,5,5,7-tetramethyl-[1,4]diazepan-2-one (314)

The title compound was prepared as described by Pyong-nae Son, J. T. Lai.: J. Org. Chem. 46, 323 (1981) for 1-butyl-3,3,5,5,7-pentamethyl-[1,4]diazepan-2-one, but using methylethylketon instead of acetone.

Colorless oil, $^1$H-NMR ($CDCl_3$), δ(ppm): 4.15–3.79 m (1H), 3.21–2.89 m ($CH_2$), 1.7–0.6 m (26H).

Example C15

1-Butyl-3-ethyl-3,5,5,7-tetramethyl-[1,4]diazepan-2-one-4-oxyl (315)

In analogy to Example B40, the compound (314) is transformed into the title compound as a red oil.

Example C16

1-Butyl-3-ethyl-4-(α-methylbenzyloxy)-3,5,5,7-tetramethyl-[1,4]diaze-pan-2-one (316)

In analogy to Example B10, the compound (315) is transformed into the title compound as a colorless oil.

$^1$H-NMR (CDCl$_3$), δ(ppm): 7.33–7.10 m (5 ArH), 4.74–4.66 m (1H), 4.40–4.34 m (1H), 3.24–3.18 m (CH$_2$), 2.3–0.5 m (29H).

The compounds prepared are summarized in Tables 1 to 3.

TABLE 1

5-ring compounds

| No. | Structure |
|---|---|
| 101 | 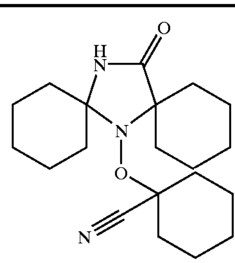 |
| 102 | 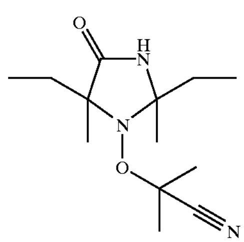 |
| 103 | 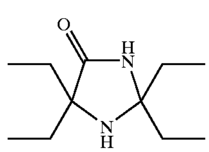 |
| 104 | 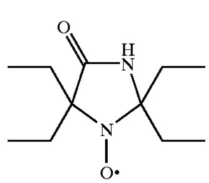 |
| 105 | |
| 106 | |

TABLE 2

6-ring compounds

| No. | Structure |
|---|---|
| 204 | 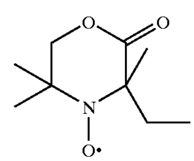 |
| 205 | 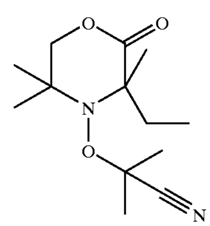 |
| 206 | 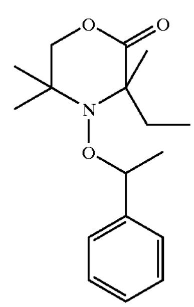 |

TABLE 2-continued 6-ring compounds

| No. | Structure |
|---|---|
| 207 | |
| 208 | |
| 209 | |
| 210 | |
| 211 | |
| 212 | |
| 213 | |
| 214 | 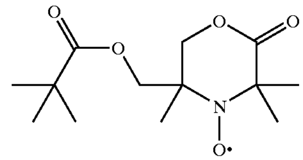 |
| 215 | 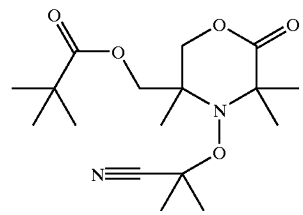 |
| 216 | 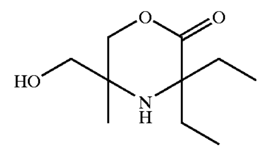 |
| 217 | 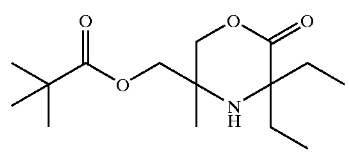 |
| 218 | 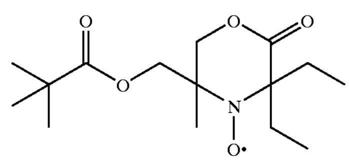 |
| 219 | 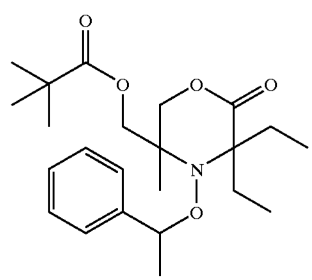 |
| 220 | 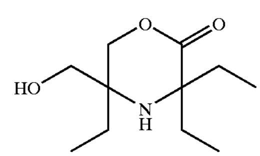 |
| 221 | 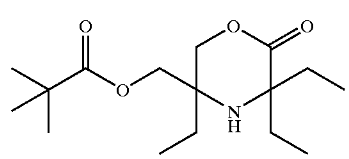 |

TABLE 2-continued 6-ring compounds

| No. | Structure |
|---|---|
| 222 | 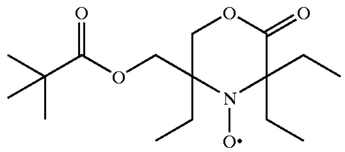 |
| 223 | 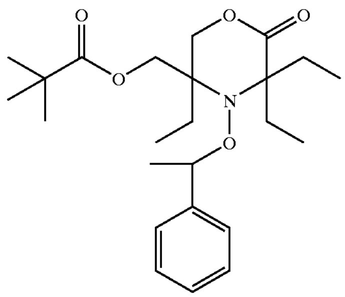 |
| 229 | 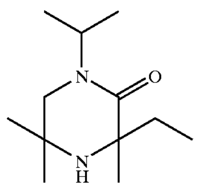 |
| 230 | 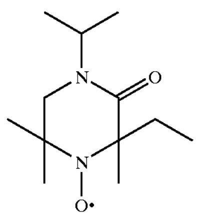 |
| 231 | 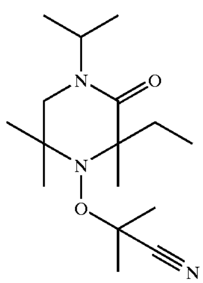 |
| 232 | 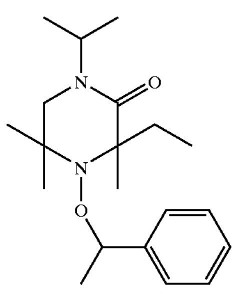 |
| 233 | |
| 234 | |
| 235 | |
| 236 | |
| 237 | |
| 238 | |

TABLE 2-continued 6-ring compounds

| No. | Structure |
|-----|-----------|
| 239 | 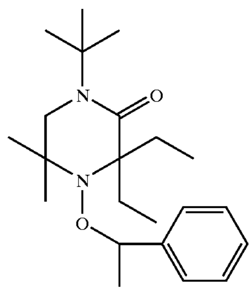 |
| 240 | 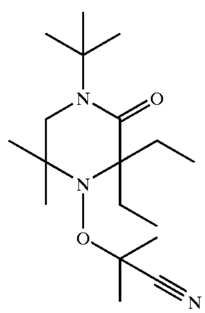 |
| 241 | 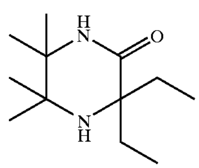 |
| 242 | 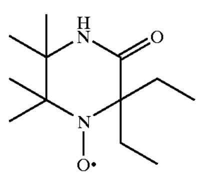 |
| 243 | 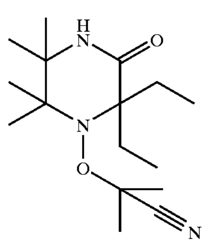 |
| 244 | 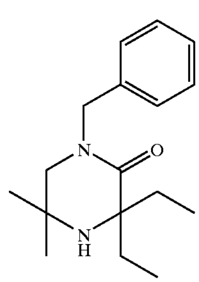 |
| 245 | |
| 246 | |
| 247 | |
| 248 | |
| 249 | |
| 250 | |

TABLE 2-continued 6-ring compounds

| No. | Structure |
|-----|-----------|
| 251 | 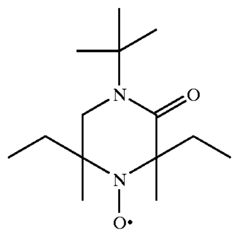 |
| 252 | 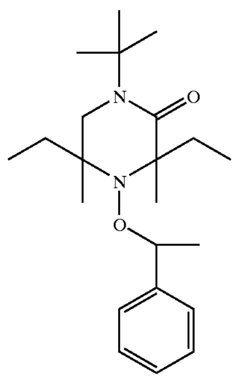 |
| 253 | 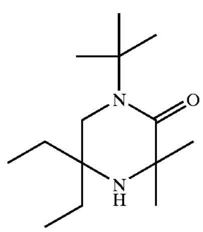 |
| 254 | 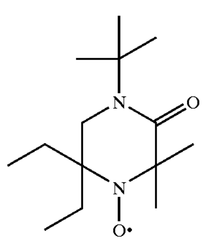 |
| 255 | 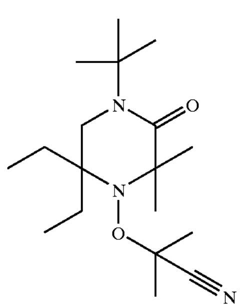 |
| 256 | |
| 257 | |
| 258 | |
| 259 | |
| 260 | |

TABLE 2-continued 6-ring compounds

| No. | Structure |
|---|---|
| 261 | 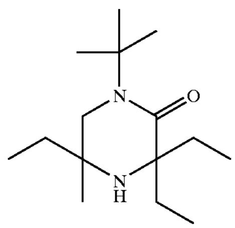 |
| 262 | 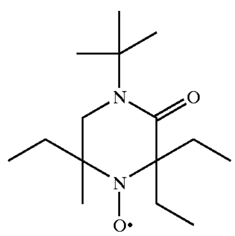 |
| 263 | 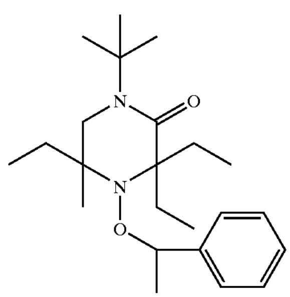 |
| 264 | 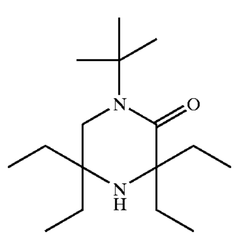 |
| 265 | 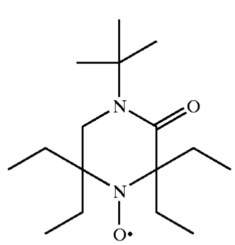 |
| 266 | |
| 267 | |
| 268 | |
| 269 | |

TABLE 2-continued
6-ring compounds
| No. | Structure |
|---|---|
| 270 | 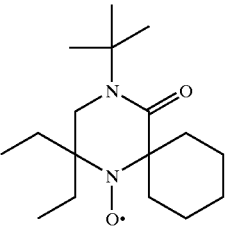 |
| 271 | 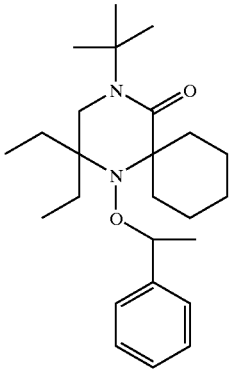 |
| 272 | 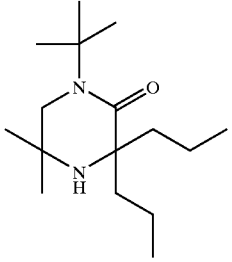 |
| 273 | 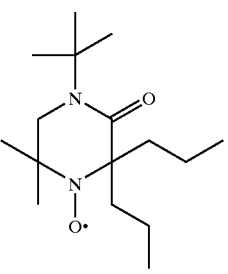 |
| 274 | 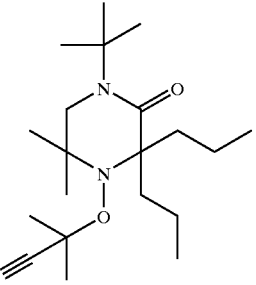 |
| 275 | 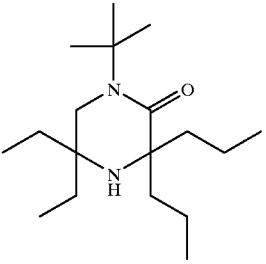 |
| 276 | 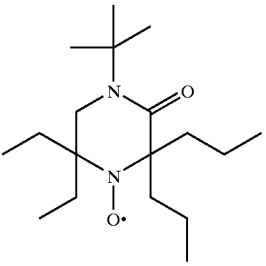 |
| 277 | 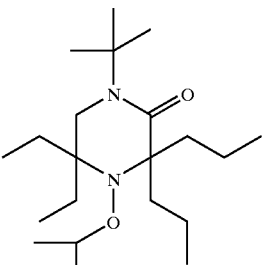 |
| 278 | 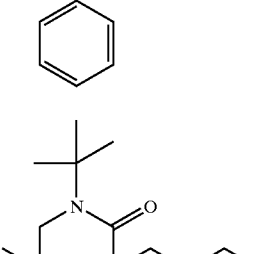 |
| 279 | 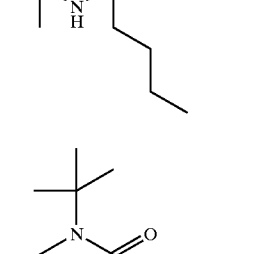 |

TABLE 2-continued 6-ring compounds

| No. | Structure |
|---|---|
| 280 | 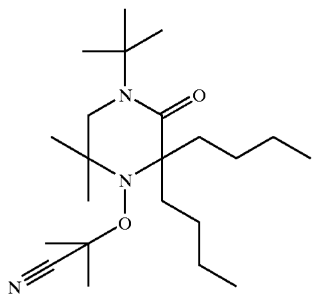 |
| 281 | 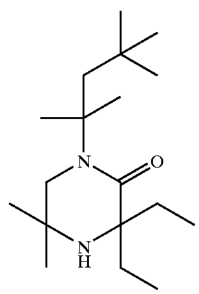 |
| 282 | 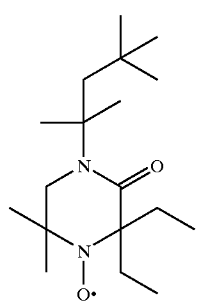 |
| 283 | 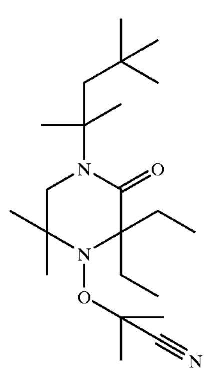 |
| 284 | |
| 285 | |
| 286 | |
| 287 | |

TABLE 2-continued 6-ring compounds

| No. | Structure |
|---|---|
| 288 | (structure) |
| 289 | (structure) |
| 290 | (structure) |
| 291 | (structure) |
| 292 | (structure) |
| 293 | (structure) |
| 294 | (structure) |
| 295 | (structure) |

TABLE 2-continued 6-ring compounds

| No. | Structure |
|---|---|
| 296 | 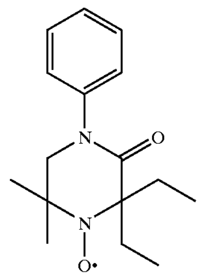 |
| 297 | 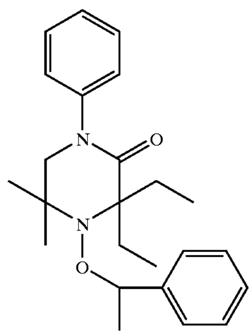 |
| 298 | 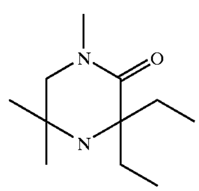 |
| 299 | 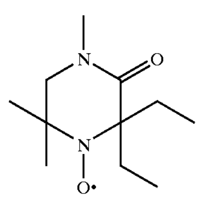 |
| 1200 | 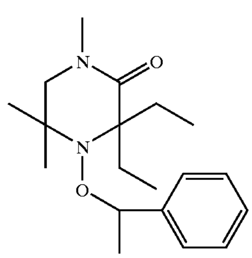 |
| 1201 | 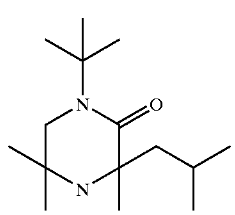 |
| 1202 | |
| 1203 | |

TABLE 3

7-ring compounds

| No. | Structure |
|---|---|
| 301 | 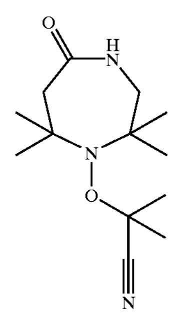 |
| 302 | 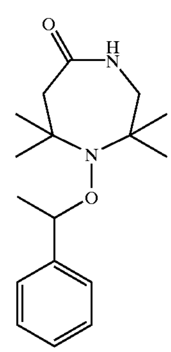 |

TABLE 3-continued 7-ring compounds

| No. | Structure |
|---|---|
| 303 | (structure) |
| 304 | (structure) |
| 305 | (structure) |
| 306 | (structure) |
| 307 | (structure) |
| 308 | (structure) |
| 309 | (structure) |
| 310 | (structure) |
| 311 | (structure) |
| 312 | (structure) |
| 313 | (structure) |

TABLE 3-continued 7-ring compounds

| No. | Structure |
|-----|-----------|
| 314 | 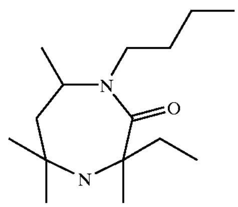 |
| 315 | 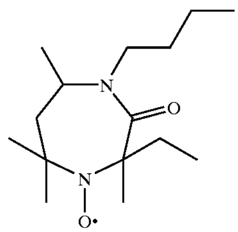 |
| 316 | 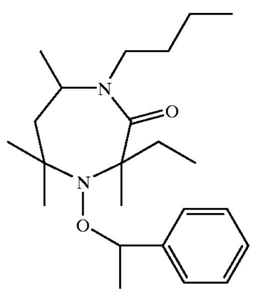 |

POLYMERIZATION EXAMPLES

Experimental runs of the polymerizations using the regulators listed in Tables 1–3:

General remarks:

Shortly before use, all solvents and monomers are distilled over a Vigreux column under argon or under vacuum.

Before polymerization, all reaction mixtures are freed from oxygen by rinsing with argon using the thaw/freeze technique and are then kept under argon gas.

Before the start of the polymerization reaction, the reagents are in the form of a clear homogeneous solution.

The monomer reaction is determined by weighing the residue after unreacted monomer has been evaporated at 80° C. and 0.02 torr over some hours until a constant weight is reached and drawing off the regulator used.

The polymers are characterised by GPC (gel permeation chromatography).

MALDI-MS: the measurements are carried out on a linear TOF (time of flight)

MALDI-MS LDI-1700, of Linear Scientific Inc., Reno, USA. The matrix used is 2,5-dihydroxybenzoic acid and the laser wavelength is 337 nm.

GPC: A two-flask series pump RHEOS 4000, of FLUX INSTRUMENTS (represented by Ercatech A G, Berne, Switzerland), is used. The pump capacity is 1 ml/min. The chromatography is carried out on two series-switched PIgel 5 μm mixed-C type columns, of POLYMER INSTRUMENTS, Shropshire, UK, at 40° C. in THF. These columns are calibrated with polystyrene at Mn from 200 to 2000000. The fractions are measured using an RI detector ERC-7515A, of ERCATECH AG, at 30° C.

1-P) Controlled Polymerization of n-butylacrylate with Compound (105) at 145° C.

A 50 ml round-bottom three-neck flask, equipped with thermometer, condenser and magnetic stirrer, is charged with 329 mg (1.2 mmol) of compound (106) and 10 g (78 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 2 g (20%) of the monomer are reacted and a clear, colourless, viscous liquid is obtained.

GPC: Mn=1500, Mw=2000, polydispersity molecular weight distribution=1.3

2-P) Controlled Polymerization of n-butylacrylate with Compound (106) at 145° C.

A 50 ml round-bottom three-neck flask, equipped with thermometer, condenser and magnetic stirrer, is charged with 373 mg (1.2 mmol) of compound (107) and 10 g (78 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 5.8 g (58%) of the monomer are reacted and a clear, colourless, viscous liquid is obtained.

GPC: Mn=5000, Mw=8900, polydispersity molecular weight distribution =1.8

3-P) Controlled Polymerization of n-butylacrylate with Compound (209) at 145° C.

A 50 ml round-bottom three-neck flask, equipped with thermometer, condenser and magnetic stirrer, is charged with 471 mg (1.7 mmol) of compound (209) and 15 g (117 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 3 g (20%) of the monomer are reacted and a clear, yellow, viscous liquid is obtained.

GPC: Mn=1600, Mw=2000, polydispersity molecular weight distribution=1.25

4-P) Controlled Polymerization of n-butylacrylate with Compound (210) at 145° C.

A 50 ml round-bottom three-neck flask, equipped with thermometer, condenser and magnetic stirrer, is charged with 536 mg (1.7 mmol) of compound (210) and 15 g (117 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 11.55 g (77%) of the monomer are reacted and a clear, colourless, viscous liquid is obtained.

GPC: Mn=6300, Mw=8700, polydispersity molecular weight distribution =1.4

5-P) Controlled Polymerization of n-butylacrylate with Compound (213) at 145° C.

A 50 ml round-bottom three-neck flask, equipped with thermometer, condenser and magnetic stirrer, is charged with 780 mg (2.3 mmol) of compound (213) and 20 g (156 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 19.6 g (98%) of the monomer are reacted and a clear, colourless, viscous liquid is obtained.

GPC: Mn=6100, Mw=11700, polydispersity molecular weight distribution=1.9

6-P) Controlled Polymerization of n-butylacrylate with Compound (213) at 130° C.

A 50 ml round-bottom three-neck flask, equipped with thermometer, condenser and magnetic stirrer, is charged with 780 mg (2.3 mmol) of compound (213) and 20 g (156 mmol) of n-butylacrylate and degassed. The clear solution is then heated to 130° C. under argon. The polymerization starts spontaneously and the temperature in the vessel rises to 130° C. The mixture is stirred for 5 hours at 130° C. and is then cooled to 60° C. and the remaining monomer is evaporated under high vacuum. 18 g (90%) of the monomer are reacted and a clear, colourless, viscous liquid is obtained.

GPC: Mn=7500, Mw=11000, polydispersity molecular weight distribution=1.45

7-P) Controlled Polymerization of n-butylacrylate with Compound (213) at 120° C.

A 50 ml round-bottom three-neck flask, equipped with thermometer, condenser and magnetic stirrer, is charged with 780 mg (2.3 mmol) of compound (213) and 20 g (156 mmol) of n-butylacrylate and degassed. The clear solution is then heated to 120° C. under argon. The polymerization starts spontaneously and the temperature in the vessel rises to 120° C. The mixture is stirred for 5 hours at 120° C. and is then cooled to 60° C. and the remaining monomer is evaporated under high vacuum. 10.4 g (52%) of the monomer are reacted and a clear, colourless, viscous liquid is obtained.

GPC: Mn=5000, Mw=6750, polydispersity molecular weight distribution=1.35

8-P) Controlled Polymerization of n-butylacrylate with Compound (219) at 145° C.

A 50 ml round-bottom three-neck flask, equipped with thermometer, condenser and magnetic stirrer, is charged with 949 mg (2.3 mmol) of compound (219) and 20 g (156 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 18.6 g (93%) of the monomer are reacted and a clear, colourless, viscous liquid is obtained.

GPC: Mn=6500, Mw=14500, polydispersity molecular weight distribution=2.2

9-P) Controlled Polymerization of n-butylacrylate with Compound (219) at 130° C.

A 50 ml round-bottom three-neck flask, equipped with thermometer, condenser and magnetic stirrer, is charged with 949 mg (2.3 mmol) of compound (219) and 20 g (156 mmol) of n-butylacrylate and degassed. The clear solution is then heated to 130° C. under argon. The polymerization starts spontaneously and the temperature in the vessel rises to 130° C. The mixture is stirred for 5 hours at 130° C. and is then cooled to 60° C. and the remaining monomer is evaporated under high vacuum. 18.6 g (93%) of the monomer are reacted and a clear, colourless, viscous liquid is obtained.

GPC: Mn=7100, Mw=16200, polydispersity molecular weight distribution=2.3

10-P) Controlled Polymerization of n-butylacrylate with Compound (219) at 120° C.

A 50 ml round-bottom three-neck flask, equipped with thermometer, condenser and magnetic stirrer, is charged with 4740 mg (1.2 mmol) of compound (219) and 10 g (78 mmol) of n-butylacrylate and degassed. The clear solution is then heated to 120° C. under argon. The polymerization starts spontaneously and the temperature in the vessel rises to 120° C. The mixture is stirred for 5 hours at 120° C. and is then cooled to 60° C. and the remaining monomer is evaporated under high vacuum. 8.7 g (87%) of the monomer are reacted and a clear, colourless, viscous liquid is obtained.

GPC: Mn=8100, Mw=17700, polydispersity molecular weight distribution=2.2

11-P) Controlled Polymerization of n-butylacrylate with Compound (223) at 145° C.

A 50 ml round-bottom three-neck flask, equipped with thermometer, condenser and magnetic stirred, is charged with 982 mg (2.3 mmol) of compound (223) and 20 g (156 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 18.6 g (93%) of the monomer are reacted and a clear, colourless, viscous liquid is obtained.

GPC: Mn=6600, Mw=10300, polydispersity molecular weight distribution=1.56

12-P) Controlled Polymerization of n-butylacrylate with Compound (231) at 145° C.

A 50 ml round-bottom three-neck flask, equipped with thermometer, condenser and magnetic stirrer, is charged with 502 mg (1.7 mmol) of compound (231) and 15 g (117 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 3.3 g (22%) of the monomer are reacted and a clear, colourless, viscous liquid is obtained.

GPC: Mn=2000, Mw=2500, polydispersity molecular weight distribution=1.2

13-P) Controlled Polymerization of n-butylacrylate with Compound (232) at 145° C.

A 50 ml round-bottom three-neck flask, equipped with thermometer, condenser and magnetic stirrer, is charged with 565 mg (1.7 mmol) of compound (232) and 15 g (117 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 11.1 g (74%) of the monomer are reacted and a clear, colourless, viscous liquid is obtained.

GPC: Mn=6000, Mw=13200, polydispersity molecular weight distribution=2.2

14-P) Controled Polymerization of n-butylacrylate with Compound (235) at 145° C.

A 50 ml round-bottom three-neck flask, equipped with thermometer, condenser and magnetic stirrer, is charged with 543 mg (1.7 mmol) of compound (235) and 15 g (117 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 7.95 g (53%) of the monomer are reacted and a clear, colourless, viscous liquid is obtained.

GPC: Mn=4500, Mw=5200, polydispersity molecular weight distribution=1.15

15-P) Controlled polymerization of n-butylacrylate with compound (236) at 145° C.

A 50 ml round-bottom three-neck flask, equipped with thermometer, condenser and magnetic stirrer, is charged with 405 mg (1.2 mmol) of compound (236) and 10 g (78 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 8.1 g (81%) of the monomer are reacted and a clear, yellow, viscous liquid is obtained.

GPC: Mn=6900, Mw=8800, polydispersity molecular weight distribution=1.3

16P) Controlled Polymerization of n-butylacrylate with Compound (239) at 145° C.

A 50 ml round-bottom three-neck flask, equipped with thermometer, condenser and magnetic stirrer, is charged with 422 mg (1.2 mmol) of compound (239) and 10 g (78 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 8.1 g (81%) of the monomer are reacted and a clear, yellow, viscous liquid is obtained.

GPC: Mn=6700, Mw=8700, polydispersity molecular weight distribution=1.3

17P) Controlled Polymerization of n-butylacrylate with Compound (240) at 145° C.

A 50 ml round-bottom three-neck flask, equipped with thermometer, condenser and magnetic stirrer, is charged with 378 mg (1.2 mmol) of compound (240) and 10 g (78 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 7.4 g (74%) of the monomer are reacted and a clear, yellow, viscous liquid is obtained.

GPC: Mn=5800, Mw=7000, polydispersity molecular weight distribution=1.2

18P) Controlled Polymerization of n-butylacrylate with Compound (243) at 145° C.

A 50 ml round-bottom three-neck flask, equipped with thermometer, condenser and magnetic stirrer, is charged with 276 mg (0.9 mmol) of compound (243) and 8 g (62 mmol) of n-butylacrylate and degassed. The clear solution is then heated to 145° C. under argon. The polymerization starts spontaneously and the temperature in the vessel rises to 145° C. The mixture is stirred for 5 hours at 145° C. and is then cooled to 60° C. and the remaining monomer is evaporated under high vacuum. 5.9 g (74%) of the monomer are reacted and a clear, yellow, viscous liquid is obtained.

GPC: Mn=6700, Mw=8100, polydispersity molecular weight distribution=1.2

19P) Controlled Polymerization of Butadiene with the Compound (239)

An autoclave is charged with 6, 85 g (0,019 mol) of the compound (239) and 54,0 g (1 mol) of butadiene. The reaction mixture is then heated for 5 hours to 145° C. After cooling to room temperature the remaining butatiene is evaporated under vacuum. 4.65 g of a clear slight yellow viscous fluid is obtained.

GPC: Mn=1400 Mw=1620 Polydispersity(PD)=1.16

20P) Block Copolymer Butadiene/n-butylacrylate

In a 50 ml three neck flask, equipped with thermometer, cooler and magnetic stirrer, 1,6 g (2 mol %) of the butadiene macroinitiator from the preceding example and 10 g of n-butylacrylate are mixed. The clear solution obtained is purged with argon and stirred for 5 hours at 145° C. The reaction mixture is then cooled to 60° C. The remaining monomer is removed be evaporation under vacuum. 5.7 g (40%) of the initial monomer have reacted. A clear slight yellow viscous fluid is obtained.

GPC: Mn=4150 Mw=5670 Polydispersity(PD)=1.36

21P) Controlled Polymerization of n-butylacrylate with the Compound (249)

A 50 ml round bottom three necked flask, equipped with thermometer, condenser and magnetic stirrer is charged with 0.405 g (1.17 mmol) (1.5Mol %) of compound (249) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.2 g (72%) of the monomer are reacted and a colourless viscous liquid is obtained.

GPC: Mn=5000 Mw=13000 Polydispersity(PD)=2.6

22P) Controlled Polymerization of n-butylacrylate with the Compound (252)

A 50 ml round bottom three necked flask, equipped with thermometer, condenser and magnetic stirrer is charged with 0.422 g (1.17 mmol) of compound (252) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.0 g (70%) of the monomer are reacted and a colourless viscous liquid is obtained.

GPC: Mn 6500 Mw=8800 Polydispersity(PD)=1.35

23P) Controlled Polymerization of n-butylacrylate with the Compound (255)

A 50 ml round bottom three necked flask, equipped with thermometer, condenser and magnetic stirrer is charged with 0.378 g (1.17 mmol) of compound (255) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 5.1 g (51%) of the monomer are reacted and a colourless viscous liquid is obtained.

GPC: Mn=4650 Mw=5600 Polydispersity(PD)=1.2

24P) Controlled Polymerization of n-butylacrylate with the Compound (258) at 145° C.

A 50 ml round bottom three necked flask, equipped with thermometer, condenser and magnetic stirrer is charged with 0.395 g (1.17 mmol) of compound (258) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a colourless viscous liquid is obtained.

GPC: Mn=6400 Mw=8950 Polydispersity(PD)=1.4

25P) Controlled Polymerization of n-butylacrylate with the Compound (258) at 120° C.

A 50 ml round bottom three necked flask, equipped with thermometer, condenser and magnetic stirrer is charged with 0.395 (1.17 mmol) of compound (258) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 3.2 g (32%) of the monomer are reacted and a colourless viscous liquid is obtained.

GPC: Mn=2600 Mw=8950 Polydispersity(PD)=1.2

26P) Controlled Polymerization of n-butylacrylate with the Compound (259) at 145° C.

A 50 ml round bottom three necked flask, equipped with thermometer, condenser and magnetic stirrer is charged with 0.422 g (1.17 mmol) of compound (259) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9 g (90%) of the monomer are reacted and a colourless viscous liquid is obtained.

GPC: Mn=6900 Mw=19300 Polydispersity(PD)=2.8

27P) Controlled Polymerization of n-butylacrylate with the Compound (259) at 120° C.

A 50 ml round bottom three necked flask, equipped with thermometer, condenser and magnetic stirrer is charged with 0.422 g (1.17 mmol) of compound (259) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 5.1 g (51%) of the monomer are reacted and a colourless viscous liquid is obtained.

GPC: Mn=6100 Mw=12200 Polydispersity(PD)=2.0

28P) Controlled Polymerization of n-butylacrylate with the Compound (260) at 145° C.

A 50 ml round bottom three necked flask, equipped with thermometer, condenser and magnetic stirrer is charged with 0.438 g (1.17 mmol) of compound (260) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 6.7 g (67%) of the monomer are reacted and a colourless viscous liquid is obtained.

GPC: Mn=6000 Mw=7200 Polydispersity(PD)=1.2

29P) Controlled Polymerization of n-butylacrylate with the Compound (260) at 120° C.

A 50 ml round bottom three necked flask, equipped with thermometer, condenser and magnetic stirrer is charged with 0.438 (1.17 mmol) of compound (260) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 4.7 g (47%) of the monomer are reacted and a colourless viscous liquid is obtained.

GPC: Mn=3300 Mw=3950 Polydispersity(PD)=1.2

30P) Controlled Polymerization of n-butylacrylate with the Compound (263) at 145° C.

A 50 ml round bottom three necked flask, equipped with thermometer, condenser and magnetic stirrer is charged with 0.438 g (1.17 mmol) of compound (263) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9 g (90%) of the monomer are reacted and a colourless viscous liquid is obtained.

GPC: Mn=7700 Mw=10800 Polydispersity(PD)=1.4

31P) Controlled Polymerization of n-butylacrylate with the Compound (263) at 120° C.

A 50 ml round bottom three necked flask, equipped with thermometer, condenser and magnetic stirrer is charged with 0.438 g (1.17 mmol) of compound (263) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 2.6 g (26%) of the monomer are reacted and a colourless viscous liquid is obtained.

GPC: Mn=2500 Mw=3000 Polydispersity(PD)=1.2

32P) Controlled Polymerization of n-butylacrylate with the Compound (263) at 100° C.

A 50 ml round bottom three necked flask, equipped with thermometer, condenser and magnetic stirrer is charged with 0.438 g (1.17 mmol) of compound (263) and 10 g (78 mmol) of n-butylacrylate and degassed. The colourless solution is then heated to 100° C. under argon. The mixture is stirred for 48 hours at 100° C. and then cooled to 60° C. and the remaining monomer is evaporated under high vacuum. 5 g (50%) of the monomer are reacted and a colourless viscous liquid is obtained.

GPC: Mn=4000 Mw=5100 Polydispersity(PD)=1.3

33P) Controlled Polymerization of n-butylacrylate with the Compound (266) at 120° C.

A 50 ml round bottom three necked flask, equipped with thermometer, condenser and magnetic stirrer is charged with 0.438 g (1.17 mmol) of compound (266) and 10 g (78 mmol) of n-butylacrylate and degassed. The colourless solution is then heated to 120° C. under argon. The mixture is stirred for 1 hour at 120° C. and then cooled to 60° C. and the remaining monomer is evaporated under high vacuum. 8.5 g (85%) of the monomer are reacted and a colourless viscous liquid is obtained.

GPC: Mn=7500 Mw=14250 Polydispersity(PD)=1.9

34P) Controlled Polymerization of n-butylacrylate with the Compound (266) at 100° C.

A 50 ml round bottom three necked flask, equipped with thermometer, condenser and magnetic stirrer is charged with 0.438 g (1.17 mmol) of compound (266) and 10 g (78 mmol) of n-butylacrylate and degassed. The colourless solution is then heated to 100° C. under argon. The mixture is stirred for 5 hours at 100° C. and then cooled to 60° C. and the remaining monomer is evaporated under high vacuum. 7 g (70%) of the monomer are reacted and a colourless viscous liquid is obtained.

GPC: Mn=6000 Mw=9000 Polydispersity(PD)=1.5

35P) Controlled Polymerization of n-butylacrylate with the Compound (267) at 120° C.

A 50 ml round bottom three necked flask, equipped with thermometer, condenser and magnetic stirrer is charged with 0.455 g (1.17 mmol) of compound (267) and 10 g (78 mmol) of n-butylacrylate and degassed. The colourless solution is then heated to 120° C. under argon. The mixture is stirred for 2 hours at 120° C. and then cooled to 60° C. and the remaining monomer is evaporated under high vacuum. 8.7 g (87%) of the monomer are reacted and a colourless viscous liquid is obtained.

GPC: Mn=7100 Mw=8500 Polydispersity(PD)=1.2

36P) Controlled Polymerization of n-butylacrylate with the Compound (267) at 100° C.

A 50 ml round bottom three necked flask, equipped with thermometer, condenser and magnetic stirrer is charged with 0.455 g (1.17 mmol) of compound (267) and 10 g (78 mmol) of n-butylacrylate and degassed. The colourless solution is then heated to 100° C. under argon. The mixture is stirred for 5 hours at 100° C. and then cooled to 60° C. and the remaining monomer is evaporated under high vacuum. 8.7 g (87%) of the monomer are reacted and a colourless viscous liquid is obtained.

After 2 hours GPC: Mn=1600 Mw=2100 Polydispersity (PD)=1.3 (22% yield)

After 5 hours: GPC: Mn=2400 Mw=3100 Polydispersity (PD)=1.3 (31% yield)

37P) Controlled Polymerization of n-butylacrylate with the Compound (268) at 120° C.

A 50 ml round bottom three necked flask, equipped with thermometer, condenser and magnetic stirrer is charged with 0.411 g (1.17 mmol) of compound (268) and 10 g (78 mmol) of n-butylacrylate and degassed. The colourless solution is then heated to 120° C. under argon. The mixture is stirred for 1 hour at 120° C. and then cooled to 60° C. and the remaining monomer is evaporated under high vacuum. 7.7 g (77%) of the monomer are reacted and a colourless viscous liquid is obtained.

GPC: Mn=6500 Mw=7800 Polydispersity(PD)=1.2

38P) Controlled Polymerization of n-butylacrylate with the Compound (268) at 100° C.

A 50 ml round bottom three necked flask, equipped with thermometer, condenser and magnetic stirrer is charged with 0.411 g (1.17 mmol) of compound (268) and 10 g (78 mmol) of n-butylacrylate and degassed. The colourless solution is then heated to 100C under argon. The mixture is stirred for 5 hours at 100° C. and then cooled to 60° C. and the remaining monomer is evaporated under high vacuum. 1.7 g (17%) of the monomer are reacted and a colourless viscous liquid is obtained.

GPC: Mn=1400 Mw=1500 Polydispersity(PD)=1.1

39P) Controlled Polymerization of n-butylacrylate with the Compound (271)

A 50 ml round bottom three necked flask, equipped with thermometer, condenser and magnetic stirrer is charged with 0.469 g (1.17 mmol) of compound (271) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.5 g (75%) of the monomer are reacted and a colourless viscous liquid is obtained.

GPC: Mn=7900 Mw=10360 Polydispersity(PD)=1.3

40P) Controlled Polymerization of n-butylacrylate with the Compound (274)

A 50 ml round bottom three necked flask, equipped with thermometer, condenser and magnetic stirrer is charged with 0.411 g (1.17 mmol) of compound (274) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8.5 g (85%) of the monomer are reacted and a colourless viscous liquid is obtained.

GPC: Mn=6400 Mw=8300 Polydispersity(PD)=1.3

41P) Controlled Polymerization of n-butylacrylate with the Compound (277) at 120° C.

A 50 ml round bottom three necked flask, equipped with thermometer, condenser and magnetic stirrer is charged with 0.487 (1.17 mmol) of compound (277) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 9 g (90%) of the monomer are reacted and a colourless viscous liquid is obtained.

GPC: Mn=7300 Mw=9500 Polydispersity(PD)=1.3

42P) Controlled Polymerization of n-butylacrylate with the Compound (277) at 110° C.

A 50 ml round bottom three necked flask, equipped with thermometer, condenser and magnetic stirrer is charged with 0.487 g (1.17 mmol) of compound (277) and 10 g (78 mmol) of n-butylacrylate and degassed. The colourless solution is then heated to 110° C. under argon. The mixture is stirred for 5 hours at 110° C. and then cooled to 60° C. and the remaining monomer is evaporated under high vacuum. 7 g (70%) of the monomer are reacted and a colourless viscous liquid is obtained.

GPC: Mn=6100 Mw=7900 Polydispersity(PD)=1.3

43P) Controlled Polymerization of n-butylacrylate with the Compound (277) at 100° C.

A 50 ml round bottom three necked flask, equipped with thermometer, condenser and magnetic stirrer is charged with 0.487 g (1.17 mmol) of compound (277) and 10 g (78 mmol) of n-butylacrylate and degassed. The colourless solution is then heated to 100° C. under argon. The mixture is stirred for 48 hours at 100° C. and then cooled to 60° C. and the remaining monomer is evaporated under high vacuum. 7 g (70%) of the monomer are reacted and a colourless viscous liquid is obtained.

GPC: after 5 hours: 37% yield, Mn=3300 Mw=4300 Polydispersity(PD)=1.3 after 48 hours: 70% yield, Mn=6500 Mw=9500 Polydispersity(PD)=1.2

44P) Controlled Polymerization of n-butylacrylate with the Compound (280)

A 50 ml round bottom three necked flask, equipped with thermometer, condenser and magnetic stirrer is charged with 0.430 g (1.17 mmol) of compound (280) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.5 g (75%) of the monomer are reacted and a colourless viscous liquid is obtained.

GPC: Mn=6000 Mw=7200 Polydispersity(PD)=1.2

45P) Controlled Polymerization of n-butylacrylate with the Compound (283)

A 50 ml round bottom three necked flask, equipped with thermometer, condenser and magnetic stirrer is charged with 0.409 g (1.17 mmol) of compound (283) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7 g (70%) of the monomer are reacted and a colourless viscous liquid is obtained.

GPC: Mn=6000 Mw=7100 Polydispersity(PD)=1.2

46P) Controlled Polymerization of n-butylacrylate with the Compound (284)

A 50 ml round bottom three necked flask, equipped with thermometer, condenser and magnetic stirrer is charged with 0.487 g (1.17 mmol) of compound (284) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a colourless viscous liquid is obtained.

GPC: Mn=7500 Mw=112500 Polydispersity(PD)=1.5

47P) Controlled Polymerization of n-butylacrylate with the Compound (286)

A 50 ml round bottom three necked flask, equipped with thermometer, condenser and magnetic stirrer is charged with 0.364 g (1.17 mmol) of compound (286) and 10 g (78 mmol) of n-butylacrylate and degassed. The colourless solution is then heated to 145° C. under argon. The mixture is stirred for 12 hours at 145° C. and then cooled to 60° C. and the remaining monomer is evaporated under high vacuum. A clear slight yellow viscous liquid is obtained.

GPC:

| | | | |
|---|---|---|---|
| 5 hours: 54% yield | Mn = 4900 | Mw = 5700 | Polydispersity(PD) = 1.1 |
| 12 hours: 84% yield | Mn = 6800 | Mw = 9200 | Polydispersity(PD) = 1.4 |

48P) Controlled Polymerization of n-butylacrylate with the Compound (289)

A 50 ml round bottom three necked flask, equipped with thermometer, condenser and magnetic stirrer is charged with 0.314 g (1.17 mmol) of compound (289) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7 g (70%) of the monomer are reacted and a colourless viscous liquid is obtained.

GPC: Mn=6100 Mw=7300 Polydispersity(PD)=1.2

49P) Controlled Polymerization of n-butylacrylate with the Compound (290)

A 50 ml round bottom three necked flask, equipped with thermometer, condenser and magnetic stirrer is charged with 0.347 g (1.17 mmol) of compound (290) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9 g (90%) of the monomer are reacted and a clear slight yellow viscous liquid is obtained.

GPC: Mn=8800 Mw=15000 Polydispersity(PD)=1.7

50P) Controlled Polymerization of n-butylacrylate with the Compound (291)

A 50 ml round bottom three necked flask, equipped with thermometer, condenser and magnetic stirrer is charged with 0.346 g (1.17 mmol) of compound (291) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9.4 g (94%) of the monomer are reacted and a clear slight yellow viscous liquid is obtained.

GPC: Mn=7000 Mw=16000 Polydispersity(PD)=2.2

51P) Controlled Polymerization of n-butylacrylate with the Compound (292)

A 50 ml round bottom three necked flask, equipped with thermometer, condenser and magnetic stirrer is charged with 0.425 g (1.17 mmol) of compound (292) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8.7 g (87%) of the monomer are reacted and a clear slight yellow viscous liquid is obtained.

GPC: Mn=7200 Mw=10100 Polydispersity(PD)=1.4

52P) Controlled Polymerization of n-butylacrylate with the Compound (293) at 145° C.

A 50 ml round bottom three necked flask, equipped with thermometer, condenser and magnetic stirrer is charged with 0.471 g (1.17 mmol) of compound (293) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.2 g (72%) of the monomer are reacted and a colourless viscous liquid is obtained.

GPC: Mn=6400 Mw=9000 Polydispersity(PD)=1.4

53P) Controlled Polymerization of n-butylacrylate with the Compound (293) at 120° C.

A 50 ml round bottom three necked flask, equipped with thermometer, condenser and magnetic stirrer is charged with 0.471 g (1.17 mmol) of compound (293) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 2.8 g (28%) of the monomer are reacted and a colourless viscous liquid is obtained.

GPC: Mn=2400 Mw=3350 Polydispersity(PD)=1.4

54P) Controlled Polymerization of n-butylacrylate with the Compound (294)

A 50 ml round bottom three necked flask, equipped with thermometer, condenser and magnetic stirrer is charged with 0.373 g (1.17 mmol) of compound (294) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a colourless viscous liquid is obtained.

GPC: Mn=9900 Mw=17800 Polydispersity(PD)=1.8

55P) Controlled Polymerization of n-butylacrylate with the Compound (297)

A 50 ml round bottom three necked flask, equipped with thermometer, condenser and magnetic stirrer is charged with 0.445 g (1.17 mmol) of compound (297) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9 g (90%) of the monomer are reacted and a colourless viscous liquid is obtained.

GPC: Mn=6400 Mw=9000 Polydispersity(PD)=1.4

56P) Controlled Polymerization of n-butylacrylate with the Compound (1200)

A 50 ml round bottom three necked flask, equipped with thermometer, condenser and magnetic stirrer is charged with 0.373 g (1.17 mmol) of compound (1200) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.7 g (77%) of the monomer are reacted and a colourless viscous liquid is obtained.

GPC: Mn=7700 Mw=10800 Polydispersity(PD)=1.4

57P) Controlled Polymerization of n-butylacrylate with the Compound (1203)

A 50 ml round bottom three necked flask, equipped with thermometer, condenser and magnetic stirrer is charged with 0.438 g (1.17 mmol) of compound (1203) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 7.8 g (78%) of the monomer are reacted and a colourless viscous liquid is obtained.

GPC: Mn=7500 Mw=12750 Polydispersity(PD)=1.7

58P) Controlled Polymerization of n-butylacrylate with the Compound (304)

A 50 ml round bottom three necked flask, equipped with thermometer, condenser and magnetic stirrer is charged with 0.447 g (1.17 mmol) of compound (304) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a colourless viscous liquid is obtained.

GPC: Mn=7000 Mw=11 900 Polydispersity(PD)=1.7

59P) Controlled Polymerization of n-butylacrylate with the Compound (305)

A 50 ml round bottom three necked flask, equipped with thermometer, condenser and magnetic stirrer is charged with 0.357 g (1.17 mmol) of compound (305) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 6.5 g (65%) of the monomer are reacted and a colourless viscous liquid is obtained.

GPC: Mn=6600 Mw=9900 Polydispersity(PD)=1.5

60P) Controlled Polymerization of n-butylacrylate with the Compound (307) at 145° C.

A 50 ml round bottom three necked flask, equipped with thermometer, condenser and magnetic stirrer is charged with 0.405 g (1.17 mmol) of compound (307) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8.6 g (86%) of the monomer are reacted and a colourless viscous liquid is obtained.

GPC: Mn=7100 Mw=10600 Polydispersity(PD)=1.5

61P) Controlled Polymerization of n-butylacrylate with the Compound (307) at 120° C.

A 50 ml round bottom three necked flask, equipped with thermometer, condenser and magnetic stirrer is charged with 0.405 g (1.17 mmol) of compound (307) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 3.7 g (37%) of the monomer are reacted and a colourless viscous liquid is obtained.

GPC: Mn=3400 Mw=4400 Polydispersity(PD)=1.3

62P) Controlled Polymerization of n-Butylacrylate with the Compound (309) at 145° C.

A 50 ml round bottom three necked flask, equipped with thermometer, condenser and magnetic stirrer is charged with 0.506 g (1.17 mmol) of compound (309) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9 g (90%) of the monomer are reacted and a yellow viscous liquid is obtained.

GPC: Mn=9100 Mw=19100 Polydispersity(PD)=2.1

63P) Controlled Polymerization of n-butylacrylate with the Compound (309) at 130° C.

A 50 ml round bottom three necked flask, equipped with thermometer, condenser and magnetic stirrer is charged with 0.506 g (1.17 mmol) of compound (309) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a yellow viscous liquid is obtained.

GPC: Mn=9100 Mw=19100 Polydispersity(PD)=2.1

64P) Controlled Polymerization of n-butylacrylate with the Compound (310) at 145° C.

A 50 ml round bottom three necked flask, equipped with thermometer, condenser and magnetic stirrer is charged with 0.389 g (1.17 mmol) of compound (310) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 8 g (80%) of the monomer are reacted and a yellow viscous liquid is obtained.

GPC: Mn=10600 Mw=21200 Polydispersity(PD)=2.0

65P) Controlled Polymerization of n-butylacrylate with the Compound (310) at 130° C.

A 50 ml round bottom three necked flask, equipped with thermometer, condenser and magnetic stirrer is charged with 0.389 g (1.17 mmol) of compound (310) and 10 g (78 mmol) of n-butylacrylate and degassed. The colourless solution is then heated to 130° C. under argon. The mixture is stirred for 5 hours at 130° C. and then cooled to 60° C. and the remaining monomer is evaporated under high vacuum. 5.5 g (55%) of the monomer are reacted and a yellow viscous liquid is obtained.

GPC: Mn=5300 Mw=9000 Polydispersity(PD)=1.7

66P) Controlled Polymerization of n-butylacrylate with the Compound (313) at 145° C.

A 50 ml round bottom three necked flask, equipped with thermometer, condenser and magnetic stirrer is charged with 0.422 g (1.17 mmol) of compound (313) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9.2 g (92%) of the monomer are reacted and a colourless viscous liquid is obtained.

GPC: Mn=7900 Mw=12600 Polydispersity(PD)=1.6

67P) Controlled Polymerization of n-butylacrylate with the Compound (313) at 120° C.

A 50 ml round bottom three necked flask, equipped with thermometer, condenser and magnetic stirrer is charged with 0.422 g (1.17 mmol) of compound (313) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 4 g (40%) of the monomer are reacted and a colourless viscous liquid is obtained.

GPC: Mn=4300 Mw=6000 Polydispersity(PD)=1.4

68P) Controlled Polymerization of n-butylacrylate with the Compound (316) at 145° C.

A 50 ml round bottom three necked flask, equipped with thermometer, condenser and magnetic stirrer is charged with 0.438 g (1.17 mmol) of compound (316) and 10 g (78 mmol) of n-butylacrylate and degassed. The colourless solution is then heated to 145° C. under argon. The mixture is stirred for 5 hours at 145° C. and then cooled to 60° C. and the remaining monomer is evaporated under high vacuum. 9.2 g (92%) of the monomer are reacted and a colourless viscous liquid is obtained.

GPC: Mn=7700 Mw=11500 Polydispersity(PD)=1.5

69P) Controlled Polymerization of n-butylacrylate with the Compound (316) at 120° C.

A 50 ml round bottom three necked flask, equipped with thermometer, condenser and magnetic stirrer is charged with 0.438 g (1.17 mmol) of compound (316) and 10 g (78 mmol) of n-butylacrylate and degassed. The colourless solution is then heated to 120° C. under argon. The mixture is stirred for 5 hours at 120° C. and then cooled to 60° C. and the remaining monomer is evaporated under high vacuum. 5.3 g (53%) of the monomer are reacted and a colourless viscous liquid is obtained.

GPC: Mn=5400 Mw=7000 Polydispersity(PD)=1.3

What is claimed is:

1. A compound of formula (IIa) or (IIb)

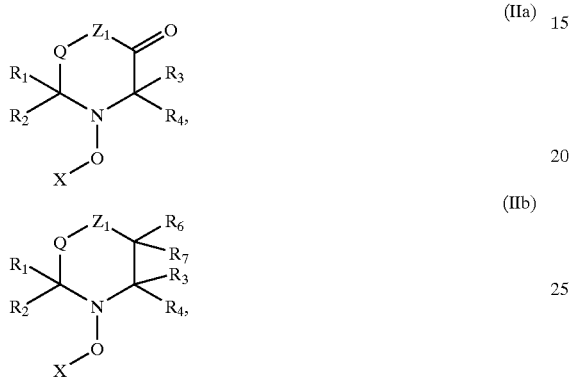

$R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;

with the proviso that if Q in formula (IIa) is —$CH_2$— or CO, at least one of $R_1$, $R_2$, $R_3$ or $R_4$ is different from methyl;

$R_5$, $R_6$ and $R_7$ independently are hydrogen, $C_1$–$C_{18}$alkyl or $C_6$–$C_{10}$aryl;

X is selected from the group consisting of —CH(aryl)$_2$, —$CH_2$-aryl,

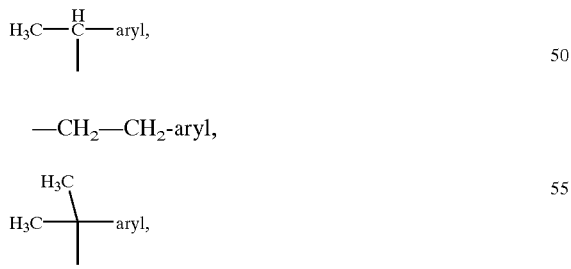

—$CH_2$—$CH_2$-aryl, ($C_5$–$C_6$cycloalkyl)$_2$CCN, $C_5$–$C_6$cycloalkylidene-CCN, ($C_1$–$C_{12}$alkyl)$_2$CCN, —$CH_2CH$=$CH_2$, ($C_1C_{12}$)alkyl-$CR_{30}$—C(O)—($C_1$-$C_{12}$)alkyl, ($C_1$-$C_{12}$)alkyl-$CR_{30}$—C(O)—($C_6$-$C_{10}$)aryl, ($C_1$-$C_{12}$)alkyl-$CR_{30}$—C(O)—($C_1C_{12}$)alkoxy, ($C_1$-$C_{12}$)alkyl-$CR_{30}$—C(O)phenoxy, ($C_1$-$C_{12}$)alkyl-$CR_{30}$—C(O)—N-di($C_1$-$C_{12}$)alkyl, ($C_1$-$C_{12}$)alkyl-$CR_{30}$—CO—NH($C_1$-$C_{12}$)alkyl, ($C_1$-$C_{12}$)alkyl-$CR_{30}$—CO—$NH_2$, —$CH_2CH$=$CH$—$CH_3$, —$CH_2$—$C(CH_3)$=$CH_2$, —$CH_2$—CH=CH-phenyl,

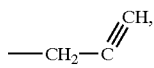

—O—C(O)—$C_1$-$C_{12}$alkyl, —O—C(O)—($C_6$–$C_{10}$)aryl, ($C_1$–$C_{12}$)alkyl-$CR_{30}$-CN,

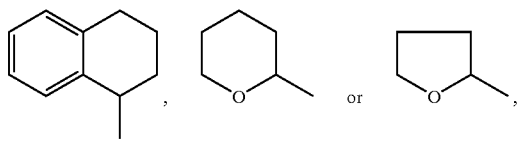

wherein $R_{30}$ is hydrogen or $C_1$–$C_{12}$alkyl;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_5$, $C_2$–$C_{18}$alkyl which is interrupted by least one O atom and/or $NR_5$ group, $C_3$–$C_{12}$cycloalkyl or $C_6$–$C_{10}$alkyl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl, and the aryl groups are phenyl or naphthyl which are unsubstituted or substituted with $C_1$–$C_{12}$alkyl, halogen, $C_1$–$C_{12}$alkoxy, $C_1$–$C_{12}$alkylcarbonyl, glycidyloxy, OH, —COOH or —COO$C_1$–$C_{12}$alkyl.

2. A compound according to claim 1 of formula (IId), (IIe), (IIf), (IIg) or (IIh)

-continued (IIg)
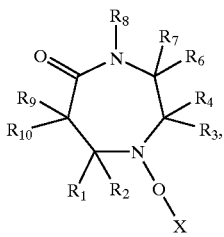

(IIh)
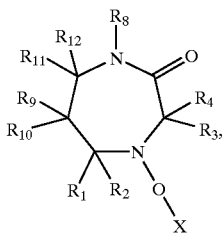

wherein $R_1$ to $R_{12}$ have the meaning as defined in claim 1 and

X is selected from the group consisting of —$CH_2$—phenyl, $CH_3CH$-phenyl, $(CH_3)_2C$-phenyl, $(CH_3)_2CCN$, —$CH_2CH$=$CH_2$, $CH_3CH$—$CH$=$CH_2$ and O—C(O)-phenyl.

3. A compound of formula (IIIa) or (IIIb)

(IIIa)
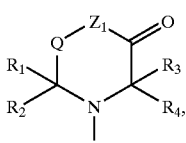

(IIIb)
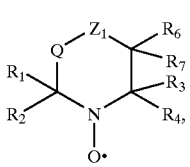

wherein $R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2C_{18}$alkyl which is interrupted by at least one O atom and/or $NR_5$ group, $C_3$–$C_{12}$cycloalkyl or $C_6$–$C_{10}$aryl or $R_1$ and $R_2$ and/or $R_3$ and $R_4$ together with the linking carbon atom form a $C_3$–$C_{12}$cycloalkyl radical;

$R_5$, $R_6$ and $R_7$ independently are hydrogen, $C_1$–$C_{18}$alkyl or $C_6$–$C_{10}$aryl;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2C_{18}$alkyl which is interrupted by at least one O atom and/or $NR_5$ group, $C_3$–$C_{12}$cycloalkyl or $C_6$–$C_{10}$aryl, $C_7C_9$phenylalkyl, $C_5C_{10}$heteroaryl, —C(O)—$C_1$–$C_{18}$alkyl, —O—$C_1$–$C_{18}$alkyl or —COO$C_1$–$C_{18}$alkyl;

Q is a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl;

with the proviso that in formula (IIIa)

if Q is $CH_2$ and $Z_1$ is O, at least one of $R_1$, $R_2$, $R_3$ or $R_4$ is higher alkyl than methyl;

or if Q is $CH_2$ or C(O) and $Z_1$ is $NR_8$ at least two of $R_1$, $R_2$, $R_3$ or $R_4$ are higher alkyl than methyl or one is higher alkyl than methyl and $R_1$ and $R_2$ or $R_3$ and $R_4$ form a $C_3$–$C_{12}$cycloalkyl radical together with the linking carbon atom.

4. A compound according to claim 3, wherein $R_1$, $R_2$, $R_3$ and $R_4$ independently of each other are $C_1$–$C_4$alkyl, which is unsubstituted or substituted by OH or a group —O—C(O)—$R_5$;

$R_5$ is hydrogen or $C_1$–$C_4$alkyl;

$R_6$ and $R_7$ independently are hydrogen, methyl or ethyl;

$Z_1$ is O or $NR_8$;

Q is a divalent radical $CH_2$, $CH_2CH_2$, $CH_2$—$CH_2$—$CH_2$, C(O), $CH_2C(O)$ or $CH_2$—CH—$CH_3$;

$R_8$ is hydrogen, $C_1$–$C_4$alkyl or $C_1$–$C_4$alkyl which is substituted by OH, or benzyl.

5. A compound of formula (IVa) or (IVb)

(IVa)
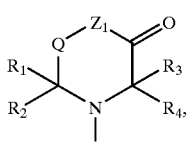

(IVb)
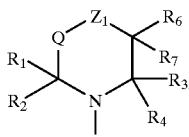

wherein $R_1$, $R_2$, $R_3$ and $R_4$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—$R_5$, $C_2C_{18}$alkyl which is interrupted by at least one O atom and/or $NR_5$ group, $C_3$–$C_{12}$cycloalkyl or $C_6$–$C_{10}$aryl;

$R_5$, $R_6$ and $R_7$ independently are hydrogen, $C_1$–$C_{18}$alkyl or $C_6$–$C_{10}$aryl;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3C_{18}$alkenyl, $C_3$–$C_{18}$alkinyl which are substituted by one or more OH, halogen or a group —O—C(O)—$R_5$, $C_2C_{18}$alkyl which is interrupted by at least one O atom and/or $NR_5$ group, $C_3$–$C_{12}$cycloalkyl or $C_6$–$C_{10}$aryl, $C_7C_9$phenylalkyl, $C_5C_{10}$heteroaryl, —C(O)—$C_1$–$C_{18}$alkyl, —O—$C_1$–$C_{18}$alkyl or —COO$C_1$–$C_{18}$alkyl;

Q is a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$, wherein $R_9$, $R_{10}$, $R_{11}$, $R_{12}$, $R_{13}$ and $R_{14}$ are independently hydrogen, phenyl or $C_1$–$C_{18}$alkyl;

with the proviso that if the compounds of formula (IVa) or (IVb) represent a 6 or 7 membered ring at least two of $R_1$, $R_2$, $R_3$ and $R_4$ are different from methyl and the substitution patterns $R_1$, $R_2$, $R_3$, $R_4$ being; methyl, methyl, butyl, butyl or methyl, ethyl, methyl, ethyl are excluded.

6. A compound according to claim 5, wherein $R_1$, $R_2$, $R_3$ and $R_4$ independently of each other are $C_1$–$C_4$alkyl, which is unsubstituted or substituted by OH or a group —O—C(O)—$R_5$;

$R_5$ is hydrogen or $C_1$–$C_4$alkyl;

$R_6$ and $R_7$ independently are hydrogen, methyl or ethyl;

$Z_1$ is O or $NR_8$;

Q is a divalent radical $CH_2$, $CH_2CH_2$, $CH_2$—$CH_2$—$CH_2$, C(O), $CH_2C(O)$ or $CH_2$—CH—$CH_3$;

$R_8$ is hydrogen, $C_1$–$C_4$alkyl or $C_1$–$C_4$alkyl which is substituted by OH, or benzyl.

7. A compound according to claim 5 wherein at least three of $R_1$, $R_2$, $R_3$ and $R_4$ are different from methyl.

8. A compound according to claim 1, wherein in formula (IIa) and (IIb) $R_1$, $R_2$, $R_3$ and $R_4$ independently of each other are $C_1$–$C_6$alkyl, which is unsubstituted or substituted by OH, halogen or a group —O—C(O)—$R_5$, $C_2$–$C_{12}$alkyl which is interrupted by at least one O atom and/or $NR_5$ group, $C_5$–$C_6$cycloalkyl or $C_6$–$C_{10}$aryl or $R_1$ and $R_2$ and/or $R_3$ and $R_4$ together with the linking carbon atom form a $C_5$–$C_6$cycloalkyl radical.

9. A compound according to claim 1, wherein in formula (IIa) and (IIb) $R_1$, $R_2$, $R_3$ and $R_4$ independently of each other are $C_1$–$C_4$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical; and $R_5$ is hydrogen or $C_1$–$C_4$alkyl.

10. A compound according to claim 1, wherein in formula (IIb) $R_6$ and $R_7$ independently are hydrogen, methyl or ethyl.

11. A compound according to claim 1, wherein in formula (IIa) and (IIb) $R_8$ is hydrogen, $C_1$–$C_{18}$alkyl, $C_1$–$C_{18}$alkyl which is substituted by OH; or $C_7C_9$phenylalkyl.

12. A compound according to claim 1, wherein in formula (IIa) and (IIb) $R_8$ is hydrogen, $C_1$–$C_4$alkyl, $C_1$–$C_4$alkyl which is substituted by OH; phenyl or benzyl.

13. A compound according to claim 1, wherein in formula (IIa) and (IIb) $R_9$, $R_{10}$, $R_{11}$, $R_{12}$, $R_{13}$ and $R_{14}$ are independently hydrogen or $C_1$–$C_4$alkyl.

14. A compound according to claim 1, wherein in formula (IIa) and (IIb) Q is a divalent radical $CH_2$, $CH_2$—$CH_2$, $CH_2$—$CH_2$—$CH_2$, C(O) or $CH_2C(O)$, $CH_2$—CH—$CH_3$, $CH_2$—CH-phenyl, phenyl-CH—$CH_2$—CH-phenyl, phenyl-CH—$CH_2$—CH—$CH_3$, $CH_2$—CH(CH)$_3$—$CH_2$, $C(CH_3)_2$—$CH_2$—CH-phenyl or $C(CH_3)_2$—$CH_2$—CH—$CH_3$.

15. A compound according to claim 1, wherein in formula (IIa) and (IIb) X is selected from the group consisting of —$CH_2$-phenyl, $CH_3CH$-phenyl, $(CH_3)_2$C-phenyl, $(CH_3)_2$CCN, —$CH_2CH$=$CH_2$, $CH_3CH$—CH=$CH_2$ and O—C(O)-phenyl.

16. A compound according to claim 1, wherein in formula (IIa) and (IIb) $R_1$, $R_2$, $R_3$ and $R_4$ independently of each other are $C_1$–$C_3$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical;

$R_5$ is hydrogen or $C_1$–$C_4$alkyl;

$R_6$ and $R_7$ independently are hydrogen, methyl or ethyl;

$Z_1$ is O or $NR_8$;

Q is a divalent radical $CH_2$, $CH_2CH_2$, $CH_2$—$CH_2$—$CH_2$, C(O), $CH_2C(O)$ or $CH_2$—CH—$CH_3$;

$R_8$ is hydrogen, $C_1$–$C_4$alkyl, $C_1$–$C_4$alkyl which is substituted by OH, or benzyl; and X is selected from the group consisting of $CH_2$-phenyl, $CH_3CH$-phenyl, $(CH_3)_2$C-phenyl, $(CH_3)_2$CCN, $CH_2CH$=$CH_2$, $CH_3CH$—CH=$CH_2$.

17. A compound according to claim 1, wherein in formula (IIa) and (IIb) at least two of $R_1$, $R_2$, $R_3$ and $R_4$ are ethyl, propyl or butyl and the remaining are methyl; or $R_1$ and $R_2$ or $R_3$ and $R_4$ together with the linking carbon atom form a $C_5$–$C_6$cycloalkyl radical and one of the remaining substituents is ethyl, propyl or butyl.

18. A compound according to claim 2, wherein the compound is of formula (IId), (IIe), (Ig) or (Ih).

19. A compound according to claim 2, wherein $R_1$, $R_2$, $R_3$ and $R_4$ independently of each other are $C_1$–$C_3$alkyl, which is unsubstituted or substituted by OH, or a group —O—C(O)—$R_5$, or $R_1$ and $R_2$ and/or $R_3$ and $R_4$ together with the linking carbon atom form a $C_5$–$C_6$cycloalkyl radical;

$R_5$ is hydrogen or $C_1$–$C_4$alkyl;

$R_6$ and $R_7$ independently are hydrogen, methyl or ethyl;

$R_8$ is hydrogen, $C_1$–$C_4$alkyl, $C_1$–$C_4$alkyl which is substituted by OH, or benzyl;

$R_9$, $R_{10}$, $R_{11}$ and $R_{12}$ are independently hydrogen or $C_1$–$C_4$alkyl; and X is selected from the group consisting of $CH_2$-phenyl, $CH_3CH$-phenyl, $(CH_3)_2$C-phenyl, $(CH_3)_2$CCN, $CH_2CH$=$CH_2$, $CH_3CH$—CH=$CH_2$.

20. A compound according to claim 2, wherein the compound is of formula (IIe);

$R_1$, $R_2$, $R_3$ and $R_4$ independently of each other are $C_1$–$C_3$alkyl, which is unsubstituted or substitute by OH, or a group —O—C(O)—$R_5$, $R_5$ is hydrogen or $C_1$–$C_4$alkyl;

$R_8$ is hydrogen, $C_1$–$C_4$alkyl, $C_1$–$C_4$alkyl which is substituted by OH, or benzyl;

$R_9$ and $R_{10}$ are hydrogen; and

X is selected from the group consisting of $CH_2$-phenyl, $CH_3CH$-phenyl, $(CH_3)_2$C-phenyl, $(CH_3)_2$CCN, $CH_2CH$=$CH_2$, $CH_3CH$—CH=$CH_2$.

21. A compound according to claim 3 wherein the compound is of formula (IIId), (IIIe), (IIIf), (IIIg) or (IIIh)

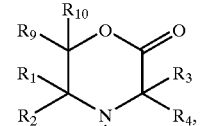

(IIId)

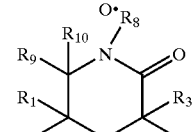

(IIIe)

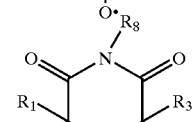

(IIIf)

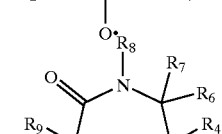

(IIIg)

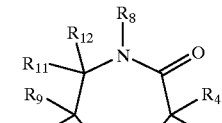

(IIIh)

* * * * *